(12) United States Patent
Haga et al.

(10) Patent No.: US 7,751,041 B2
(45) Date of Patent: Jul. 6, 2010

(54) FLUORESCENCE DETECTION APPARATUS

(75) Inventors: Takanobu Haga, Kokubunji (JP);
Satoshi Takahashi, Hitachinaka (JP);
Nobutaka Kumazaki, Hitachinaka (JP);
Hirokazu Kato, Mito (JP); Tsuyoshi Sonehara, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/339,285

(22) Filed: Dec. 19, 2008

(65) Prior Publication Data
US 2009/0168061 A1 Jul. 2, 2009

(30) Foreign Application Priority Data
Dec. 27, 2007 (JP) .............................. 2007-335612

(51) Int. Cl.
*G01J 3/30* (2006.01)
(52) U.S. Cl. ........................ 356/317; 356/417; 356/445; 356/318; 356/72; 356/73
(58) Field of Classification Search ................. 356/317, 356/318, 417, 445, 72–73; 250/458.1–461.2; 422/82.07–82.08
See application file for complete search history.

(56) References Cited

U.S. PATENT DOCUMENTS 5,341,215 A * 8/1994 Seher .......................... 356/445
7,012,693 B2 * 3/2006 Mori et al. ................... 356/445

FOREIGN PATENT DOCUMENTS

JP 8-136554 5/1996

OTHER PUBLICATIONS

I. Braslavsky, vol. 100, No. 7, Apr. 2003, pp. 3960-3964.

* cited by examiner

*Primary Examiner*—Tarifur Chowdhury
*Assistant Examiner*—Abdullahi Nur
(74) *Attorney, Agent, or Firm*—Mattingly & Malur, P.C.

(57) ABSTRACT

A fluorescent detection apparatus relates to an analysis technique for qualitatively detecting or quantifying biomolecules by producing an evanescent field on a surface of a substrate, exciting fluorescently labelled biomolecules on the substrate surface in the evanescent field, and detecting the resultant fluorescent light emitted from the biomolecules. The fluorescent detection apparatus has a configuration in which a well is provided in a surface opposing to a sample substrate of a prism, the well is filled with a matching liquid, and the matching liquid is filled between the sample substrate and the prism, thereby improving operability and providing a stable evanescent field.

22 Claims, 17 Drawing Sheets

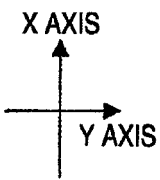
FIG.4A1  FIG.4A2
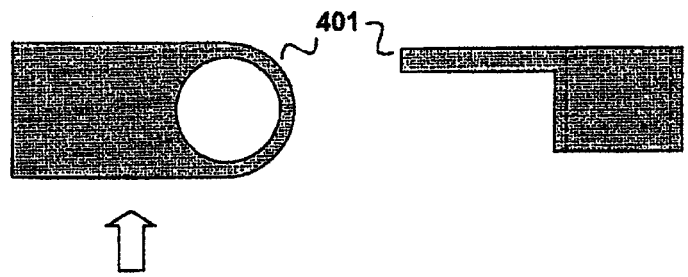
FIG.4B1  FIG.4B2
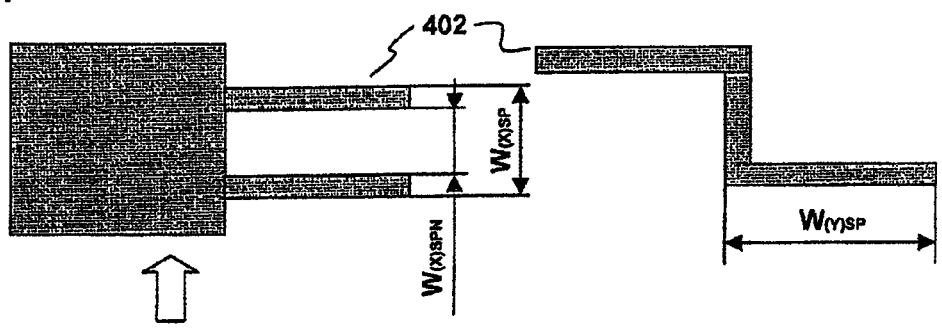
FIG.4C1  FIG.4C2
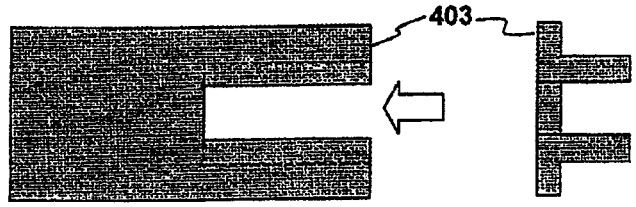

FIG.17A
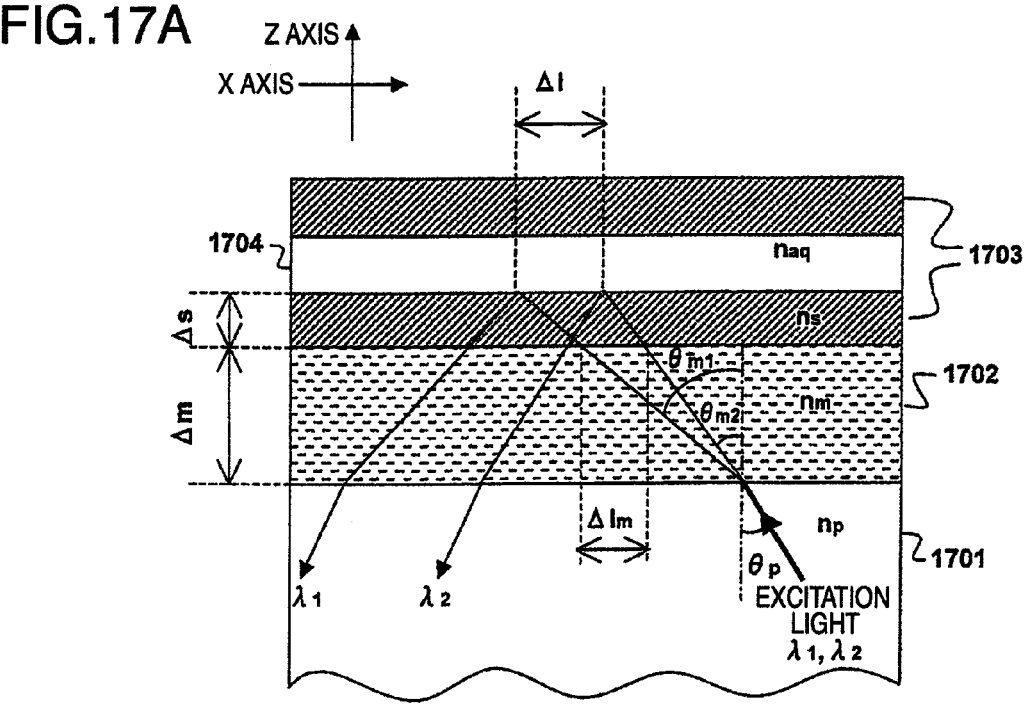
FIG.17B
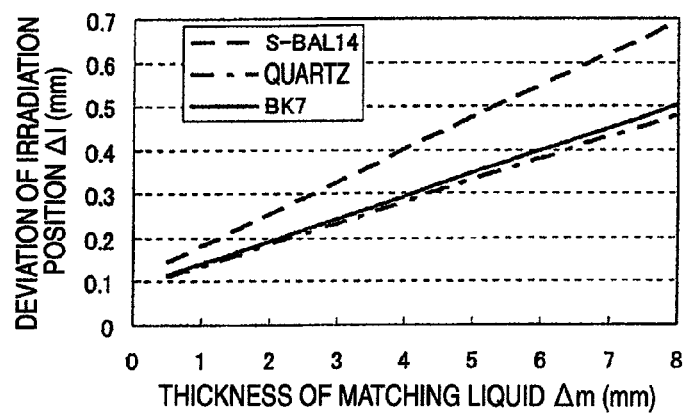
FIG.17C
| WAVELENGTH OF EXCITATION LIGHT ($\lambda$)(nm) | | 488 | 633 | INCIDENCE ANGLE $\theta_p$ |
|---|---|---|---|---|
| PRISM ($n_p$) | S-BAL14 | 1.576 | 1.566 | 57.9 |
| | QUARTZ | 1.463 | 1.457 | 65.6 |
| | BK7 | 1.522 | 1.515 | 61.0 |
| MATCHING LIQUID ($n_m$) | GLYCEROL | 1.473 | | |
| SAMPLE SUBSTRATE ($n_s$) | QUARTZ | 1.463 | 1.457 | |
| THICKNESS OF SAMPLE SUBSTRATE ($\Delta s$) | | 1mm | | |

FLUORESCENCE DETECTION APPARATUS

INCORPORATION BY REFERENCE

The present application claims priority from Japanese application JP2007-335612 filed on Dec. 27, 2007, the content of which is hereby incorporated by reference into this application.

FIELD OF THE INVENTION

The present invention relates to an analysis technique for qualitatively detecting or quantifying biomolecules by producing an evanescent field on a surface of a transparent substrate, exciting fluorescently labelled biomolecules in a liquid sample supplied on the substrate surface in the evanescent field, and detecting the resultant fluorescent light emitted from the biomolecules.

DESCRIPTION OF RELATED ART

In the related art, single fluorescent molecule has been observed using an evanescent field produced on a substrate surface by irradiating excitation light emitted from an light source to a transparent sample substrate and totally reflecting the excitation light on the surface of the sample substrate.

For example, as disclosed in "Funatsu et al., Nature Vol. 374, 555-559 (1995)", for single molecule fluorescence detection, in order to produce an evanescent field, a prism plane and a sample substrate are oppositely arranged in parallel to each other and a matching liquid for matching a refractive index of the prism plane and a refractive index of the sample substrate is filled between the prism plane and the sample substrate.

In addition, as disclosed in "Braslavsky et al., PNAS Vol. 100, 3960-3964 (2003)", sequencing single DNA molecule using a total-internal-reflection fluorescence microscopy is conducted. Here, lasers having wavelengths of 532 nm and 635 nm are used for fluorescence detection of a fluorophore Cy3 and a fluorophore Cy5, respectively. When single target DNA molecules are immobilized on a sample substrate filled with a solution using a biotin-avidin protein binding and a primer labelled with Cy3 is introduced into the solution such that the primer has constant concentration by a solution exchange, single fluorescence-marked primer molecules are hybridized with the target DNA molecules. At this time, since Cy3 exists in an evanescent field, the existence of the target DNA molecules hybridized with Cy3-labelled primer can be recognized by the fluorescence detection. After the fluorescence detection of Cy3, Cy3 is photobleached by irradiating Cy3 with excitation light of high power of 532 nm, thereby suppressing later fluorescent light emission. Next, when polymerase and dNTP (N being one of A, C, G and T), which is a kind of base labelled with Cy5 mono-molecule, are introduced in the solution such that the polymerase and the dNTP have constant concentration, respectively, by solution exchange, fluorescently labelled dNTP molecules are incorporated into elongation end of primer molecules only when the fluorescently labelled dNTP molecules have complementary relation with target DNA molecules. At this time, since Cy5 exists in an evanescent field, the incorporation can be checked at a position of the target DNA molecules by fluorescence detection. After the check, Cy5 is photobleached by irradiating Cy5 with excitation light of high power of 635 nm, thereby suppressing later fluorescent light emission. By repeating the above-described dNTP incorporating reaction process sequentially and cyclically for kinds of bases, for example, A→C→G→T→A→ (cyclic polymerase reaction), it is possible to determine a sequence having a complementary relation with the target DNA molecules. In addition, by immobilizing a plurality of target DNA molecules within the same field of a fluorescence detection image and performing the dNTP incorporating reaction process in parallel, a simultaneous DNA sequencing of the plurality of target DNA molecules becomes possible. It is expected that the number of simultaneous parallel processes at this time can rapidly increase in comparison with a conventional electrophoresis-based DNA sequencing.

In such a conventional single molecule fluorescence detection, by flowing a matching liquid onto a prism when a sample substrate is arranged, the matching liquid is filled between the sample substrate and the prism such that air is not introduced between the sample substrate and the prism. In this case, however, if the amount of the flown matching liquid is excessive, an apparatus may become dirty due to matching liquid leaked out during replacement of the sample substrate or the like, which may have an adverse effect on stage precision or measurement.

For the purpose of overcoming this problem, JP-A-8-136554 discloses a method of receiving matching liquid which overflows in replacement of a sample substrate by providing a grooved oil puddle in the outer circumference of a prism.

In the conventional single molecule fluorescence detection, when the sample substrate is arranged, it is required to fill the matching liquid between the prism and the sample substrate in such a manner that air is not introduced therebetween. In this case, if the amount of flown matching liquid is small, it becomes difficult for the sample substrate to move due to surface energy of the matching liquid. Even if the sample substrate does move, the matching liquid moves with horizontal movement of the sample substrate and air is introduced between the sample substrate and the prism, thereby preventing excitation light from arriving at the sample substrate. On the other hand, if the amount of flown matching liquid is excessive, an apparatus becomes dirty not only during replacing the sample substrate, but also when the sample substrate moves as the prism is pressed against the sample substrate. Accordingly, the matching liquid may be attached to an excitation light incident surface of the prism, thereby preventing an evanescent field from being produced.

In addition, in the method disclosed in JP-A-8-136554, if the amount of flown matching liquid is excessive, when the prism is pressed against the sample substrate or is moved with respect to the sample substrate, the matching liquid flows into the oil puddle and thus the matching liquid between the prism and the sample substrate becomes insufficient, thereby causing air to be easily introduced therebetween. On the other hand, if the amount of flown matching liquid is too small, likewise, air is likely to be introduced between the prism and the sample substrate. Accordingly, since it is required to pay attention to the amount of filling of the matching liquid and the movement of the sample substrate, the disclosed method has a problem of operability as a whole.

In this manner, the above-described conventional techniques have insufficient consideration of a structure of an apparatus with good operability which is capable of producing a stable evanescent field.

BRIEF SUMMARY OF THE INVENTION

The present invention relates to an analysis technique for qualitatively detecting or quantifying biomolecules by producing an evanescent field on a surface of a substrate, exciting fluorescently labelled biomolecules on the substrate surface in the evanescent field, and detecting the resultant fluorescence emitted from the biomolecules, and a well is provided in a surface opposing a sample substrate, and the matching liquid is filled in the well so as to involve the sample substrate in the matching liquid and fill the matching liquid between the sample substrate and the prism, thereby overcoming the above problem.

By providing the well in the surface opposing the sample substrate of the prism, it is possible to prevent the matching liquid from being leaked out and preventing an excitation light incidence surface of the prism or an apparatus from being dirty by the leaked matching liquid. In addition, since the well can be filled with the matching liquid by simply pouring the matching liquid into the well, operability can be improved.

Other objects, features and advantages of the invention will become apparent from the following description of the embodiments of the invention taken in conjunction with the accompanying drawings.

BRIEF DESCRIPTION OF SEVERAL VIEWS OF DRAWING

FIGS. 4A1 to 4C1 are views illustrating modifications of a prism supporting member B in Embodiment 1 of the invention.

FIGS. 4A2 to 4C2 are projective views viewed in arrow directions in FIGS. 4A1 to 4C1.

FIGS. 5A to 5D are conceptual views of a real time sequencing method in Embodiment 1 of the invention.

Figure 6:
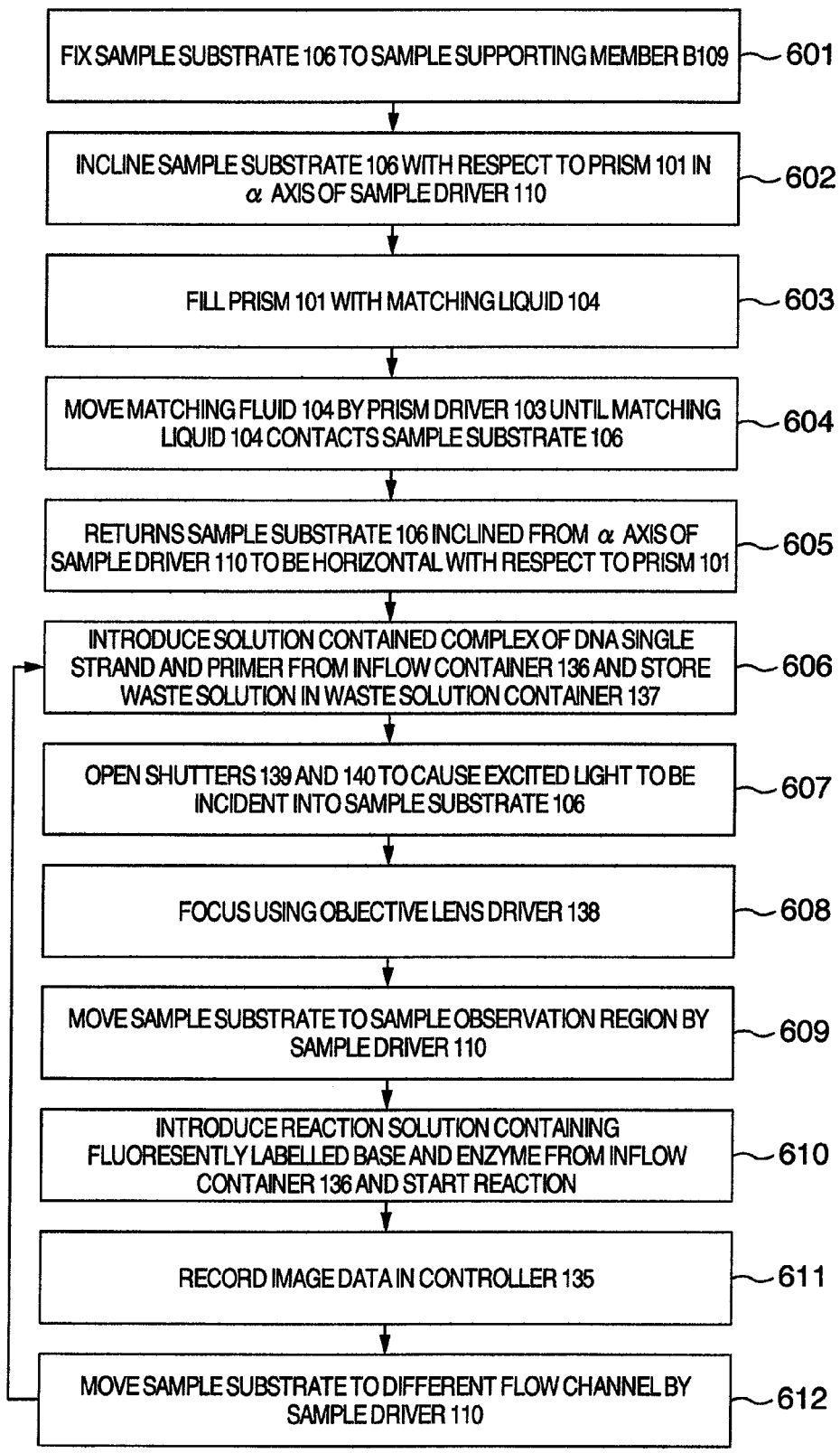

FIG. 6 is a flow chart of a measuring process in Embodiment 1 of the invention.

Figure 7:
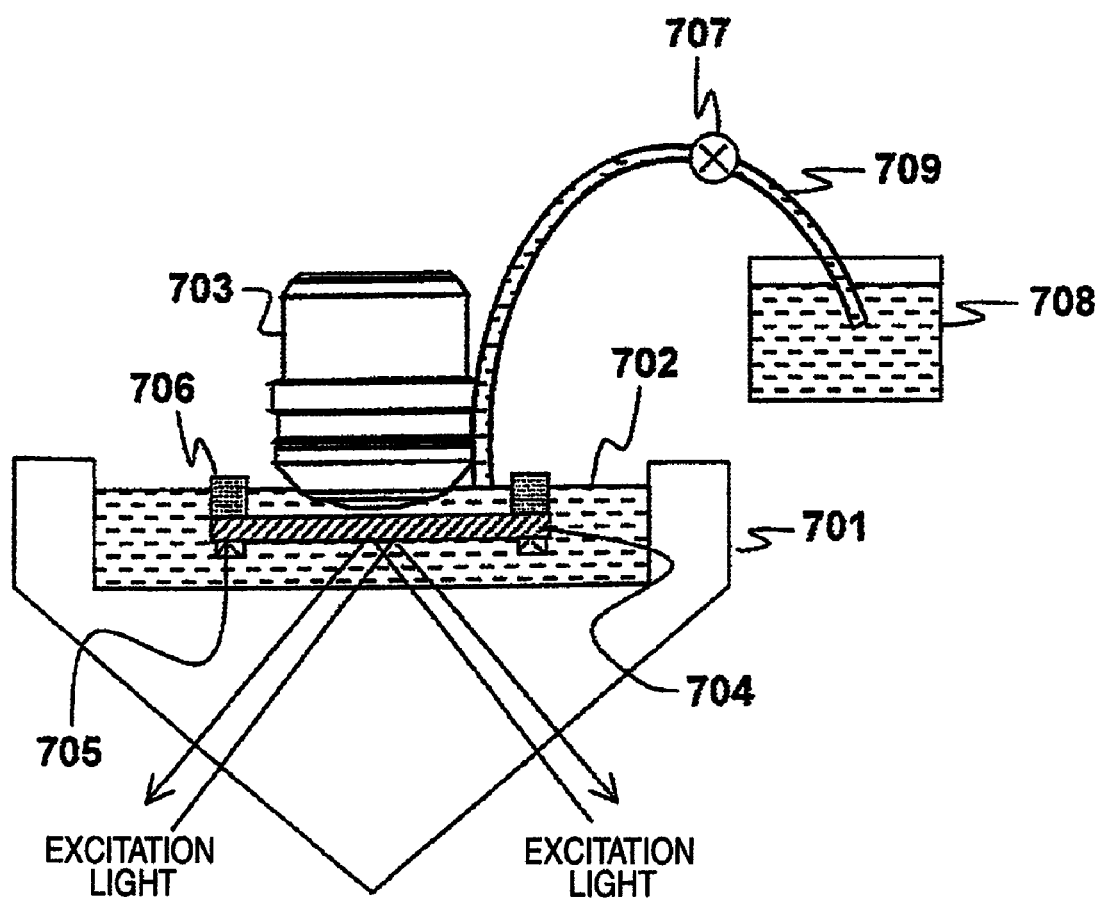

FIG. 7 is a sectional view including an excitation light path in the vicinity of a prism in Embodiment 2 according to the invention.

Figure 8A:
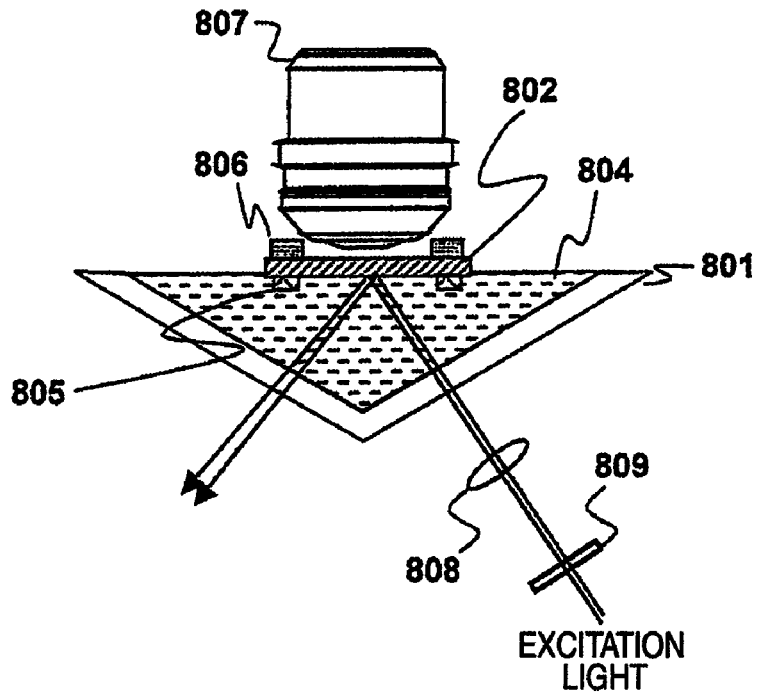
Figure 8B:
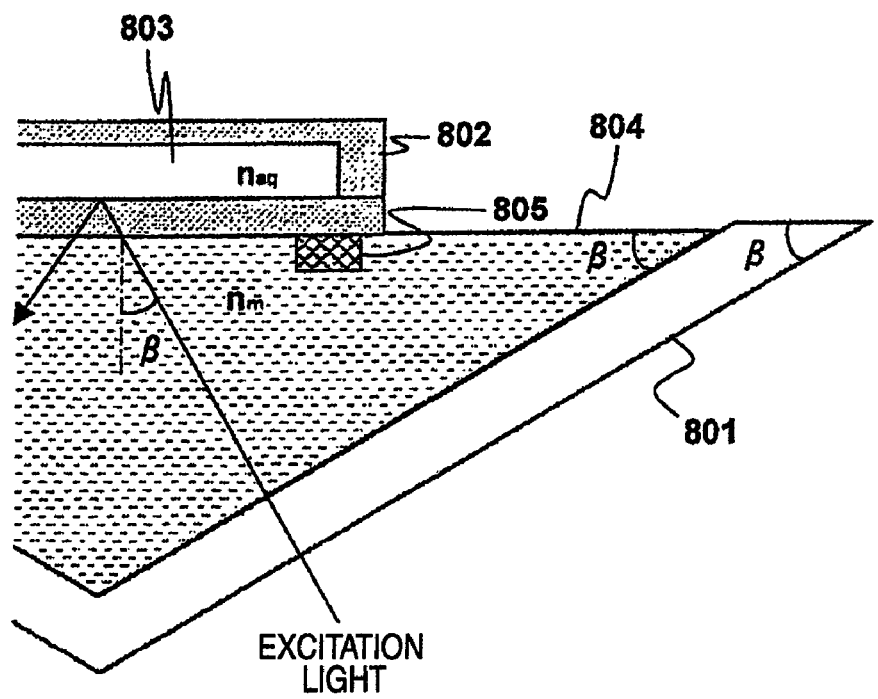

FIGS. 8A and 8B are sectional views including an excitation light path in the vicinity of a prism in Embodiment 3 according to the invention.

Figure 9A:
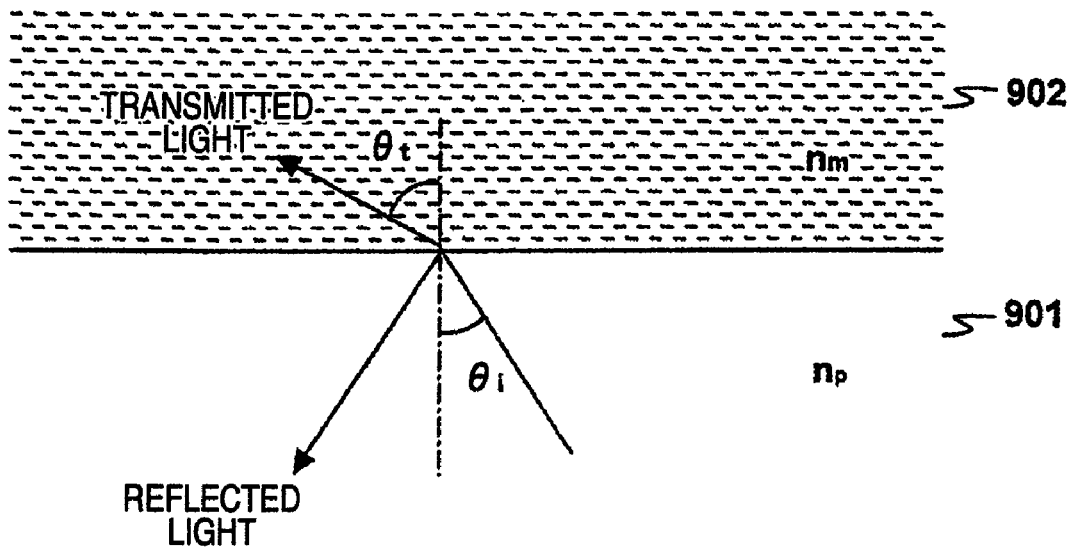

FIG. 9A is a view illustrating a form of transmission/reflection at an interface between a prism and a matching liquid in Embodiment 3 of the invention.

Figure 9B:
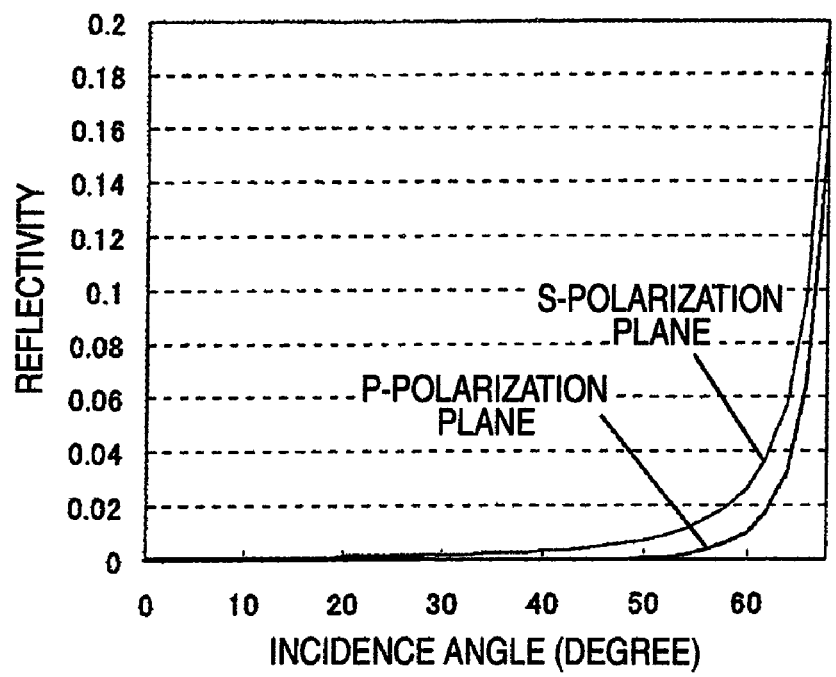

FIG. 9B is a graph illustrating a relation between an incident angle and reflectivity in Embodiment 3.

Figure 10A:
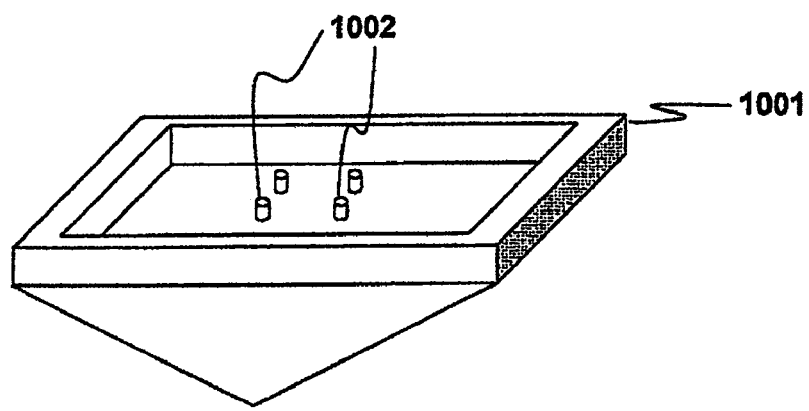

FIG. 10A is an enlarged view of a prism in Embodiment 4 according to the invention.

Figure 10B:
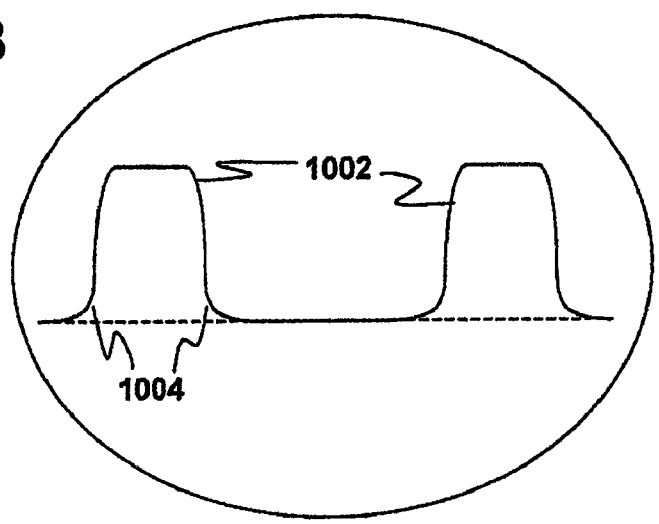

FIG. 10B is a partial sectional view of Embodiment 4 of FIG. 10A.

Figure 10C:
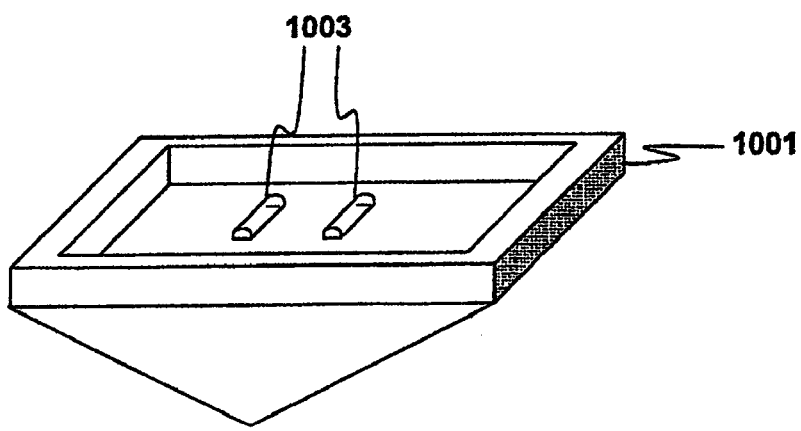

FIG. 10C is a view illustrating a modification of Embodiment 4.

Figure 11A:
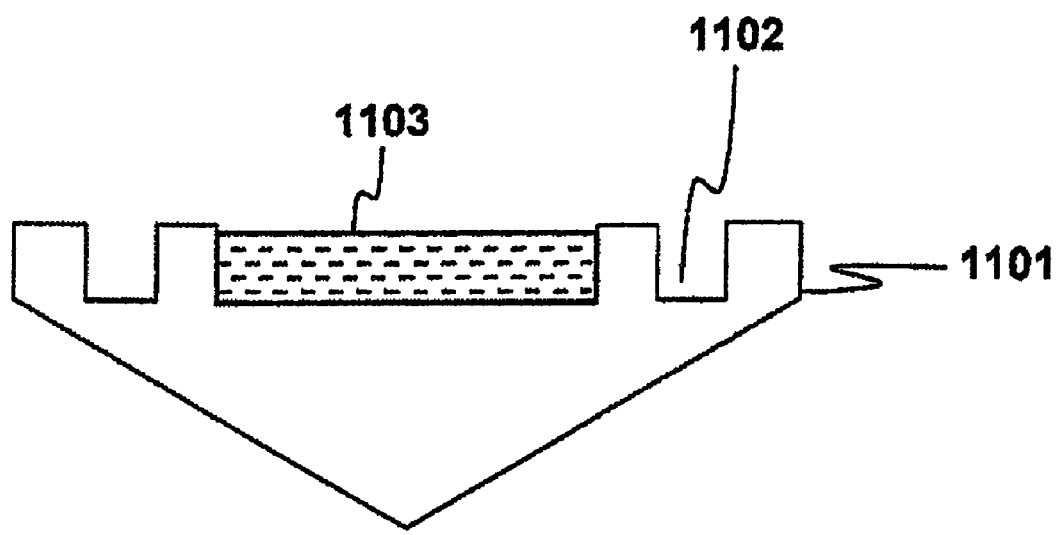
Figure 11B:
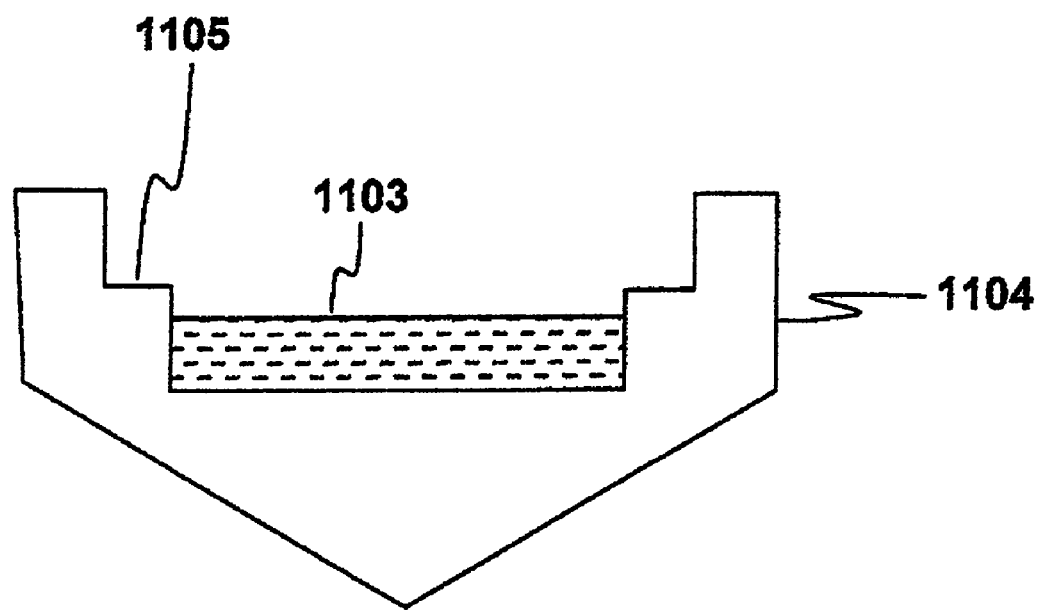

FIGS. 11A and 11B are enlarged views of a prism in Embodiment 5 according to the invention.

Figure 12:
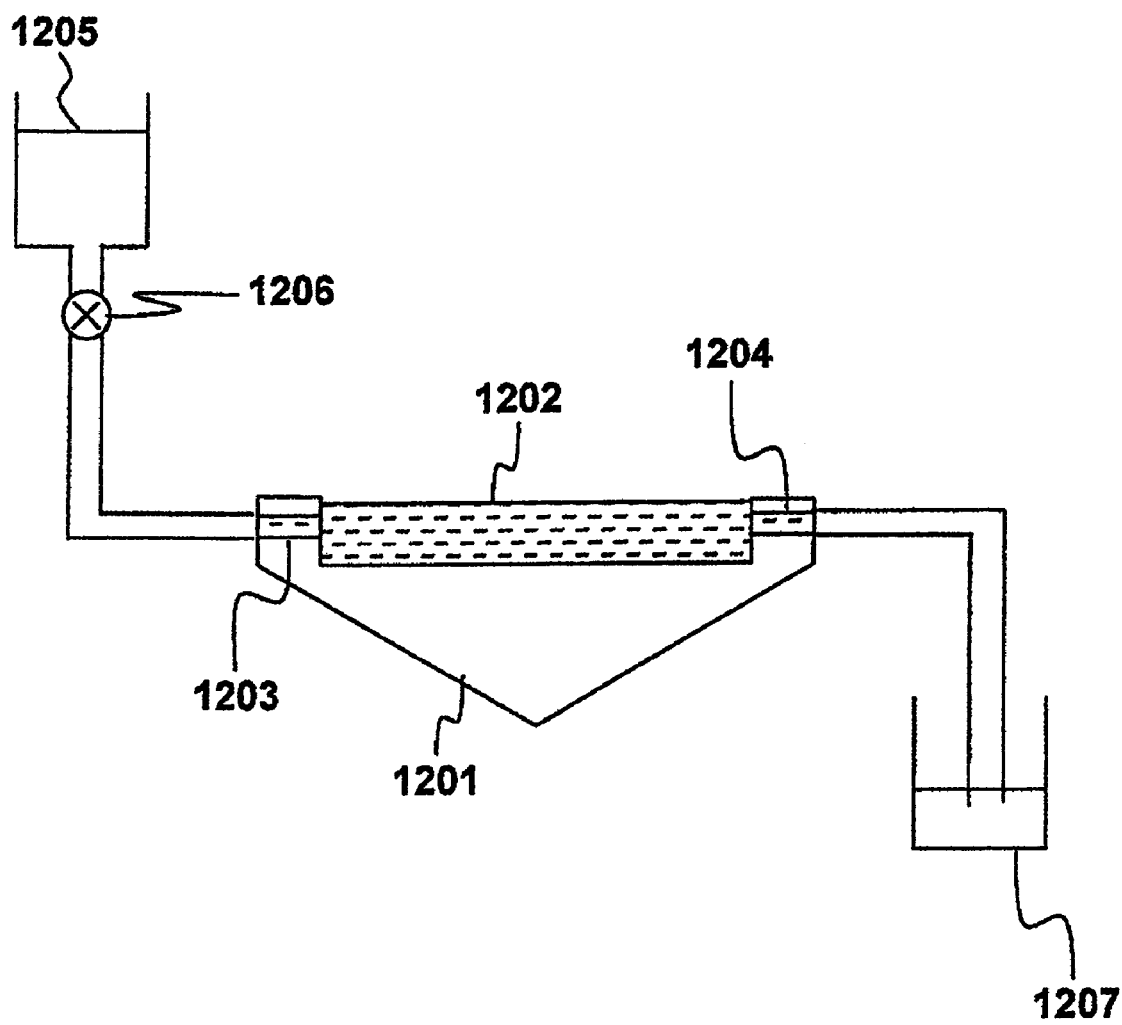

FIG. 12 is an enlarged view of the vicinity of a prism in Embodiment 6 according to the invention.

Figure 13A:
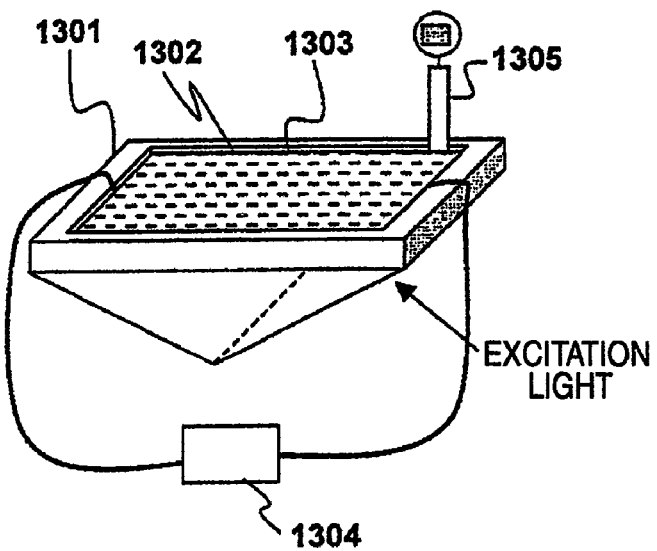
Figure 13B:
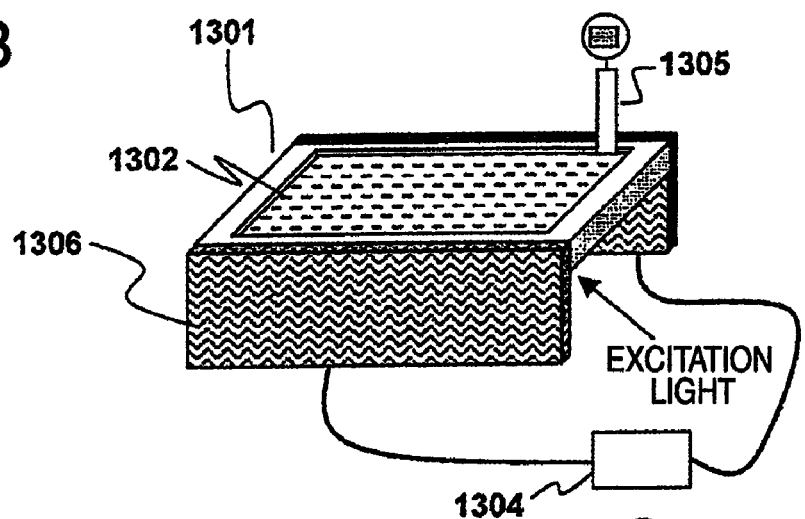
Figure 13C:
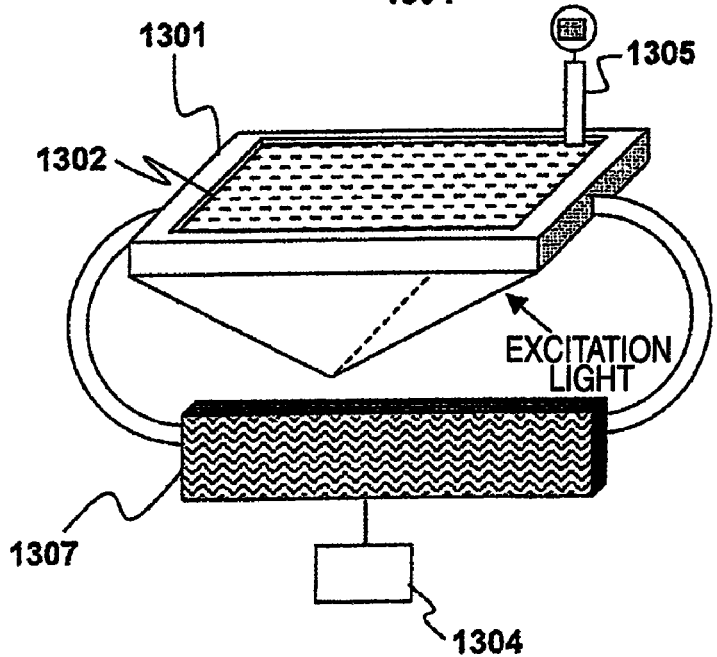

FIGS. 13A to 13C are enlarged views of the vicinity of a prism in Embodiment 7 according to the invention.

Figure 14A:
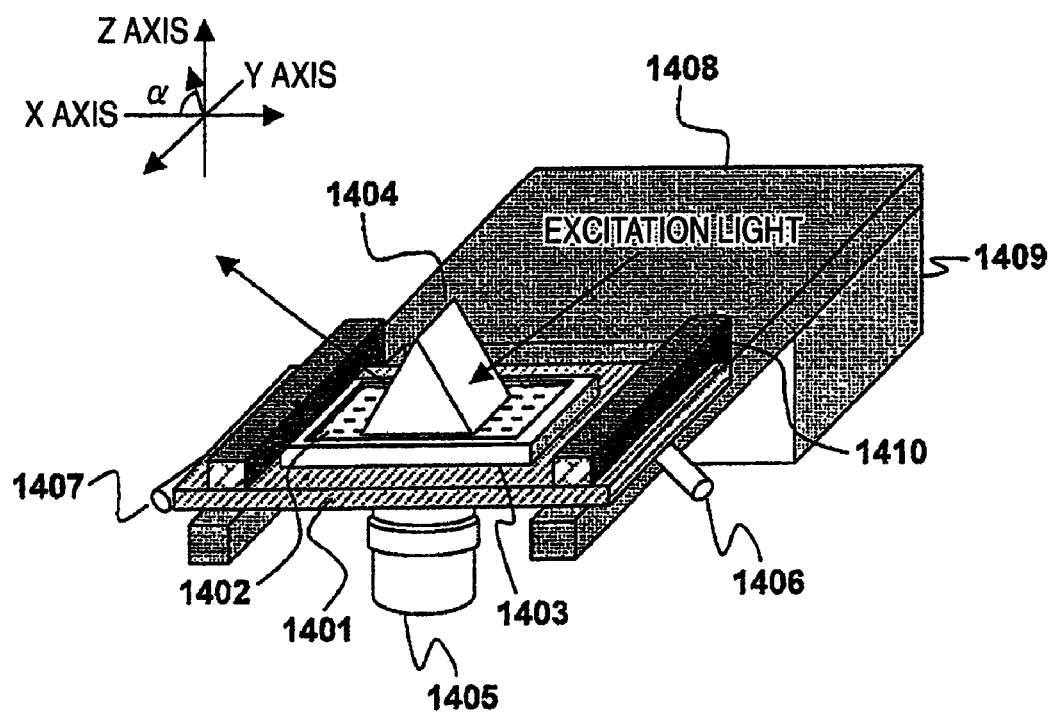
Figure 14B:
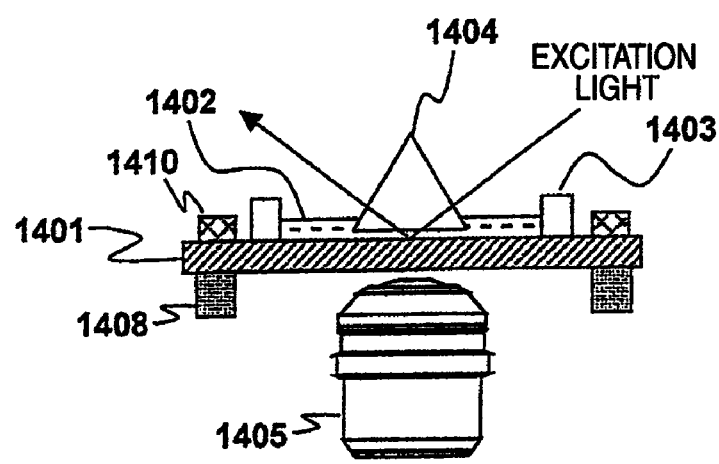

FIGS. 14A and 14B are enlarged views of the vicinity of a prism in Embodiment 8 according to the invention.

Figure 15A:
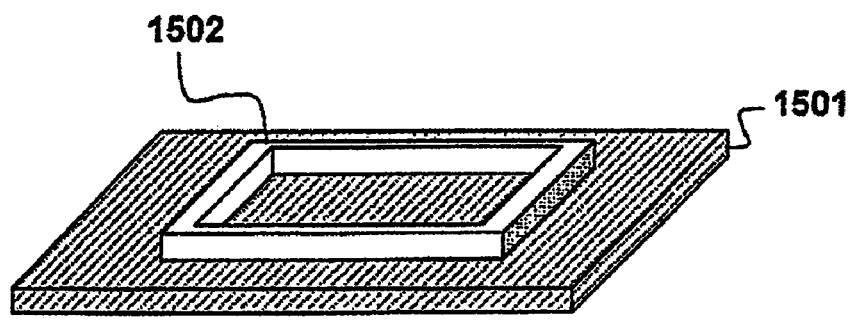
Figure 15B:
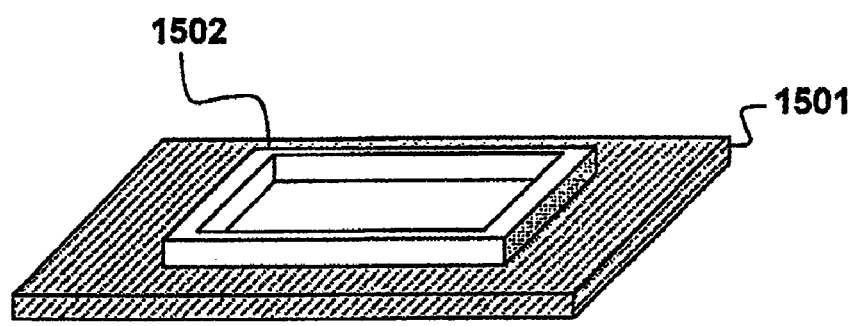
Figure 15C:
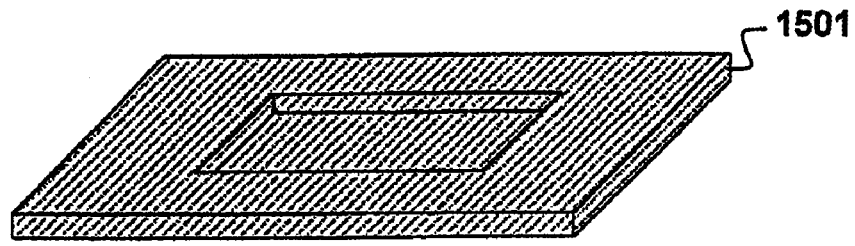

FIGS. 15A to 15C are views illustrating modifications of a shape of well formed on a sample substrate in Embodiment 8 of the invention.

Figure 16:
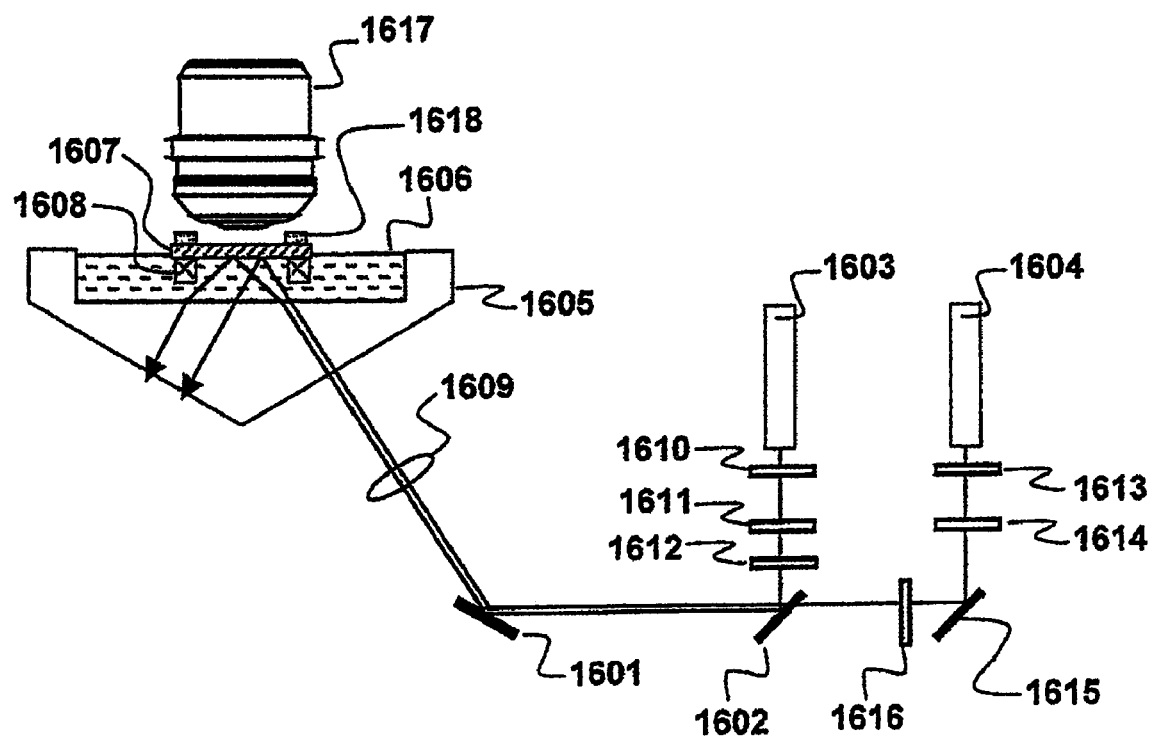

FIG. 16 is a sectional view including excitation light paths from two light sources in the vicinity of a prism when the excitation light share the same path in Embodiment 3 of the invention.

FIG. 17A is a view showing light paths after incidence of light into a matching liquid when the excitation light from two light sources share the same path in Embodiment 3 of the invention.

FIG. 17B is a graph showing a relation between thickness of a matching liquid and deviation of an evanescent irradiation position when the excitation light from two light sources share the same path in Embodiment 3.

FIG. 17C is a table showing parameter values used for calculation in FIG. 17B.

DETAILED DESCRIPTION OF THE INVENTION

Hereinafter, exemplary embodiments of the present invention will be described with reference to the accompanying drawings.

Embodiment 1

Figure 1A:
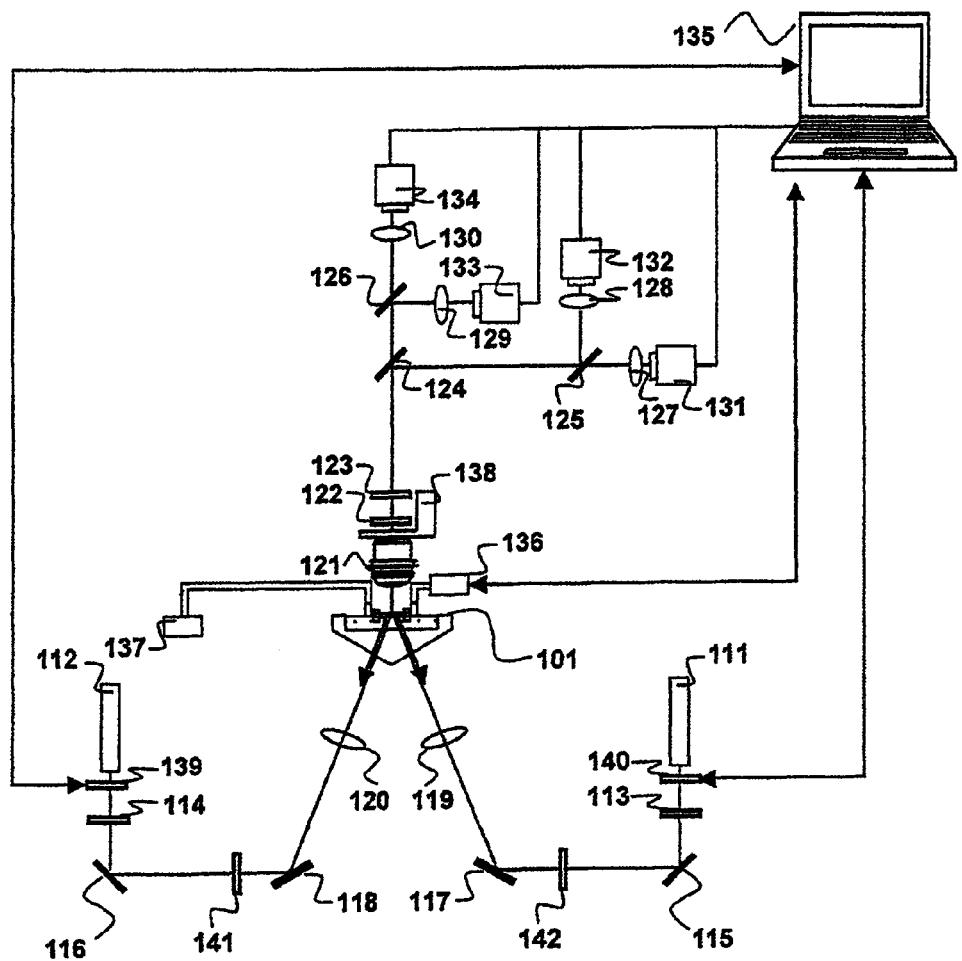
FIG. 1A is a view illustrating a configuration of Embodiment 1 according to the invention.
Figure 1B:
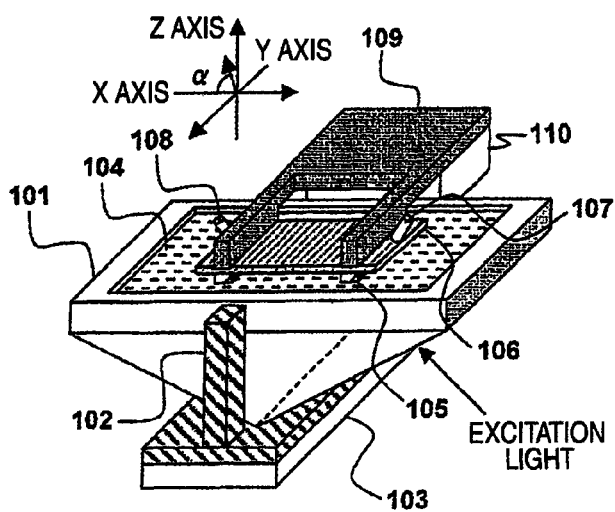
FIG. 1B is an enlarged perspective view illustrating a prism 101 and its vicinity in Embodiment 1 of the invention.
Figure 2A:
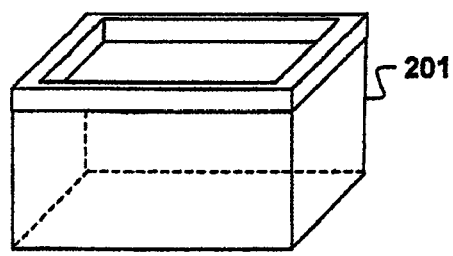
FIGS. 2A to 2E are views illustrating modifications of the prism in Embodiment 1 of the invention.
Figure 2B:
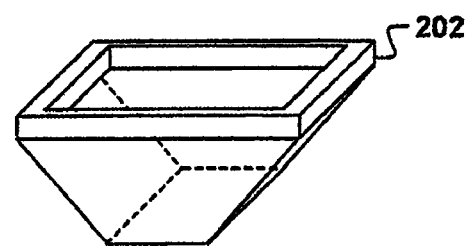
Figure 2C:
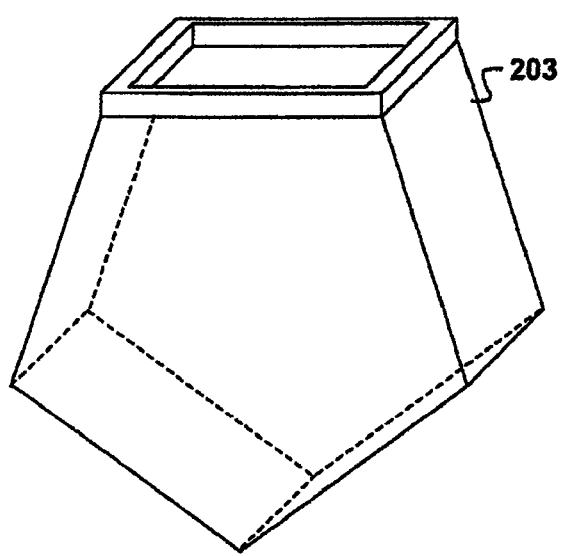
Figure 2D:
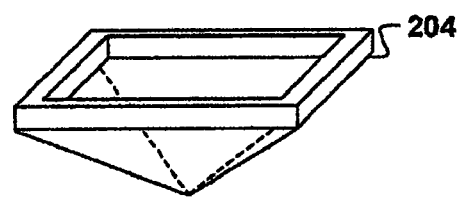
Figure 2E:
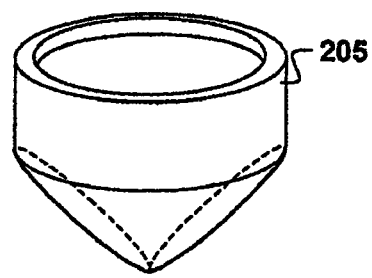

FIG. 1A is a view illustrating a configuration of Embodiment 1 according to the invention. FIG. 1B is an enlarged perspective view showing a prism 101 and its vicinity.

A prism 101 provided with a well is, for example, made of S-BAL14 and has three 60° equilateral surfaces each having a size of 60 mm×50 mm. An acryl frame having height of about 8 mm (depth of the well later), as a wall of the well, is adhered to one (surface opposed to a sample substrate 106) of the three surfaces. Aside from the above-described method, a well structure may be prepared by cutting a surface of the prism 101.

Height of the well is required to be adjusted such that a surface of the sample substrate 106 including a sample supporting member 105 which opposes the prism 101, can be immersed in a matching liquid 104. Instead of S-BAL14, the material of the prism may be glass such Bak4, quartz or the like, resin such as PDMS or the like, or other materials as long as they have low absorptiveness and self-fluorescence to an excitation wavelength.

There is no problem for the prism to have the shape shown in FIG. 1 or the shapes 201 to 205 shown in FIGS. 2A to 2E, but it is required to allow light to be incident from the prism 101 and 201 to 205 into the matching liquid 104 in such a manner that the total reflection condition expressed by the following Equation 1 is satisfied.

$$\eta_p > \sin^{-1}(n_{aq}/n_p)$$ [Equation 1]

Figure 3:
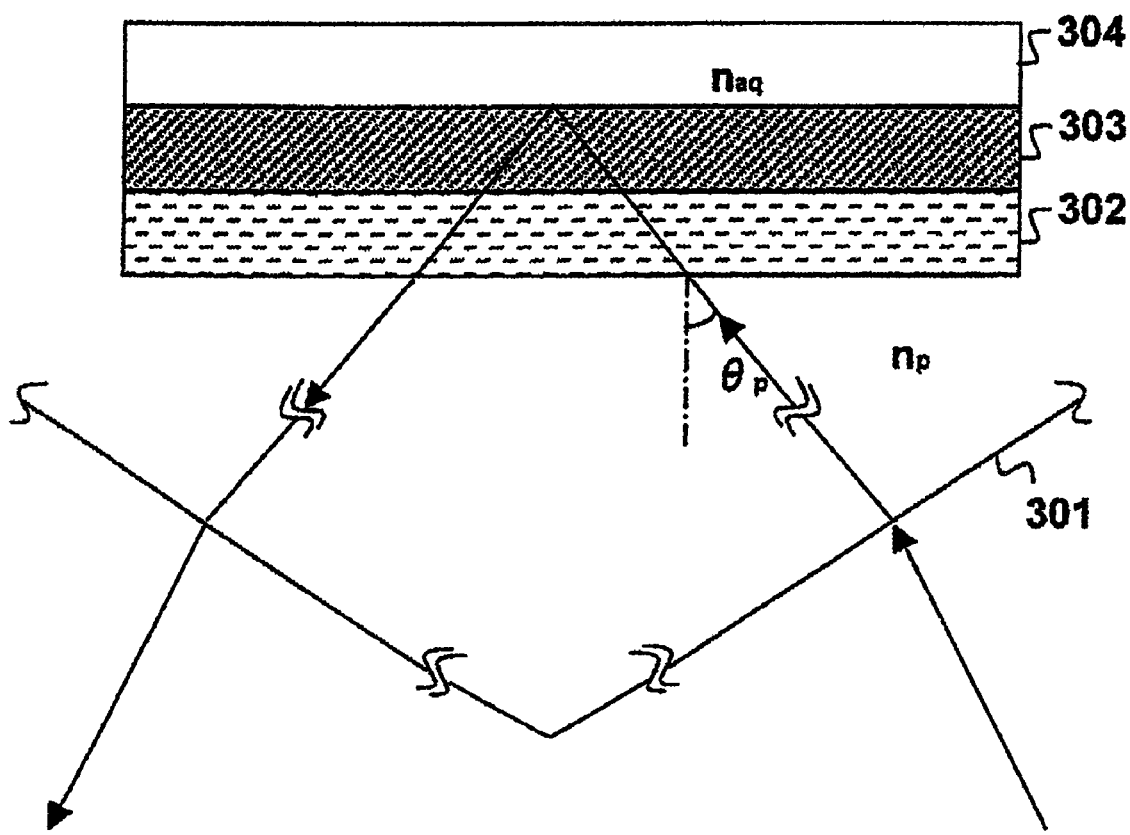
FIG. 3 is a view illustrating an angle of evanescent irradiation in Embodiment 1 of the invention.

Here, the total reflection condition of Equation 1 will be described with reference to FIG. 3. As shown in FIG. 3, $\theta_p$ represents an incidence angle from a prism 301 into a matching liquid 302, $n_{aq}$ represents a refractive index of a sample solution 304, and $n_p$ represents a refractive index of the prism 301. In this embodiment, since $n_p=1.57$ for the prism made of the material S-BAL14 and $n_{aq}=1.33$ for the sample solution 304, an incidence angle condition for total reflection according to Equation 1 becomes $\theta_p > 57.9$ degree, and the incidence angle condition is adjusted to meet this condition. If the incidence angle does not meet this condition, excitation light permeates the sample solution 304 without being totally reflected. This leads to deterioration of measurement sensitivity due to background intensity caused by Raman scattering of water, which may result in remarkable deterioration of measurement precision of single fluorescent molecule. Incidentally, the numeral 303 denotes a sample substrate.

The prism 101 is fixed to a prism driver 103 by a prism supporting member 102 and may be moved in X, Y and Z axis directions by controlling the prism driver 103 manually or automatically by a controller.

The well of the prism 101 is filled with glycerol as the matching liquid 104. As the Z axis of the prism driver 103 is moved such that the matching liquid 104 slowly approaches to the sample substrate 106, the matching liquid 104 is filled between the sample substrate 106 and the prism 101. Instead of glycerol, the matching liquid 104 may be immersion oil or the like, but preferably has a refractive index close to those of the sample substrate 106 and the prism 101 and low absorptiveness and self-fluorescence to an excitation wavelength. If there is a large difference in refractive index, a loss by excitation light reflection at an interface between the matching liquid 104 and the sample substrate 106 or prism 101 may increase, lowering the excitation strength, or reflected light may become background light in a measurement region by repeated reflection on neighboring members, thereby disturbing a measurement. In addition, if the absorptiveness and self-fluorescence to the excitation wavelength are high, an excitation power is lowered or background intensity increases by the fluorescence, thereby disturbing the measurement.

The sample substrate 106 is prepared by attaching two substrates together, one being quartz glass of 45 mm×25 mm formed on a side (lower surface) opposing to the prism 101 and another being a PDMS substrate (having the same size as the lower surface) formed with a flow channel on an upper side. The intended solution flows into an observation region within the sample substrate 106 through an inflow path 107 and an outflow path 108 which are combined with both ends of the PDMS substrate for exchange of solution. In addition, aside from the above materials, the sample substrate 106 may employ materials having absorptiveness and self-fluorescence to an excitation wavelength, which should be as low as to have no effect on a measurement. The size of the sample substrate 106 is required to be as small as to be contained in the well or the prism 101 is required to be as large as to contain the sample substrate 106.

The sample supporting member 105 is used to tightly press and fix the sample substrate 106 against a sample stage 109. This can prevent irregular deviation of a fluorescent image due to drift of the sample substrate 105 during measurement.

In this embodiment, two polycarbonate plates having thickness of 2 mm and size of 35 mm×5 mm are used for the sample supporting member 105, in each of which drill holes are formed at both ends for passing screws through. The sample substrate 106 is tightly fixed by sandwiching the sample substrate 106 between the sample supporting members and the sample stage and fastening the sample substrate 106 using screwed holes formed in the sample stage 109. Alternatively, a leaf spring or the like may be used as the sample supporting member 105. Although this shown embodiment employs a structure where the sample substrate is vertically sandwiched, the sample substrate may be held horizontally by using concave portions or the like formed in the sample supporting members and sandwiching the sample substrate from both horizontal sides in a manner to keep the sample substrate horizontal.

The sample stage 109 is fixed to the sample driver 110 movable in X, Y and α axis directions. By controlling the sample driver 110 manually, or automatically by a controller 135, the sample substrate 106 may be scanned in the X and Y axis directions or may be inclined by driving the α axis. The sample driver 110 may be further provided with an additional Z axis for use in focus adjustment in fluorescence observation. Here, the Z axis is an axis perpendicular to a surface of the matching liquid 104 and the X axis is perpendicular to the Z axis and is in parallel to a plane including an excitation light path. The Y axis is perpendicular to an X-Z plane and α is an angle defined between the X axis and the α axis in the X-Z plane.

Alternatively, the shape of the sample stage 109 may be as denoted by 401 to 403 in FIGS. 4A1-4C2. However, to avoid a physical interference of an apparatus, when the X and Y axis directions are defined as in FIG. 1, an outer width ($W_{(X)SP}$) in the X axis direction and an outer width ($W_{(Y)SP}$) in the Y axis direction of a supporting member pressing the sample substrate 106 are required to be smaller than the width of the well in the corresponding axial directions, and an inner width ($W_{(X)SPN}$) in the X axial direction is required to be larger than an outer diameter of an objective lens.

Hereinafter, the vicinity of an optical system of FIG. 1A will be described. Excitation light emitted from an excitation light source 111 or 112 increases spectrum purity through an excitation filter 113 or 114, being reflected on a mirror 115 or 116 to become circularly polarized light in a λ/4 plate 141 or 142, being reflected on an angle adjustment mirror 118 or 117, being compressed in a condensing lens 119 or 120, being incident into the prism 101, and then being incident into the sample substrate 106. The excitation light incident into the sample substrate 106 is totally reflected at an interface between the sample substrate and a sample aqueous solution to produce an evanescent field on a surface of the sample substrate 106. Emission from the surface of the sample substrate 106 excited by the evanescent field is collected and collimated in an objective lens 121 and a component (elastic scattering light) having the same wavelength as the excitation light is removed by light emitting filters 122 and 123.

Thereafter, the light is transmitted or reflected in different directions for different wavelengths in dichroic mirrors 124 to 126 and focused by imaging lenses 127 to 130 an image is formed on a photoelectric surface of each of image sensors 131 to 134. Each image obtained in the image sensors 131 to 134 is recorded in a controller 135 serving as a computer having processing, storage and control functions.

Although an Ar-ion laser having wavelengths of 488 nm and 514.5 nm is used as the excitation light source 111 and a laser diode having a wavelength of about 633 nm is used as the excitation light source 112 in this embodiment, it is to be understood that a second harmonic laser of Nd-YAG, a helium-neon laser or a semiconductor laser may be used as the excitation light source. Although a long pass filter transmitting a wavelength of 525 nm or above is used as the light emitting filter 122 and a notch filter intercepting a wavelength of 620 nm to 645 nm is used as the light emitting filter 123, it is to be understood that a band pass filter transmitting a range of wavelengths to be detected may be used as the light emitting filter as well. Although, as the dichroic mirrors 124 to 126, the dichroic mirror 124 is used to transmit wavelengths of 620 nm or above, the dichroic mirror 125 is 560 nm or above, and the dichroic mirror 126 is 690 nm or above, respectively, the dichroic mirrors 124 to 126 having different characteristics may be used to correspond to the excited wavelength and fluorescent dye used.

Figure 5A:
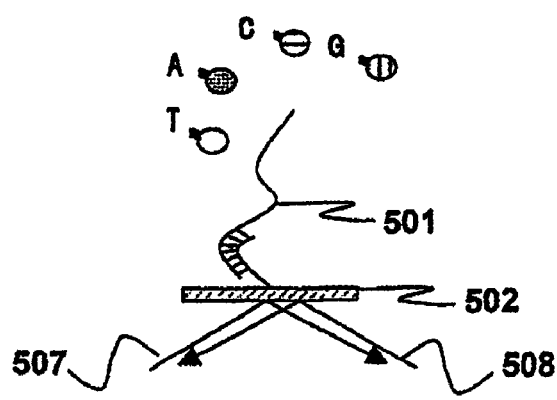

In this embodiment, using the configuration shown in FIGS. 1A and 1B, a DNA sequence is determined in real time by a method as shown in FIGS. 5A to 5D. An elongation reaction starts by developing a reaction solution containing an enzyme essential for an elongation reaction with fluorescently labelled bases 503 to 506 on a surface of the sample substrate 502 on which a complex 501 of a single DNA strand for determining a sequence and a primer is immobilized (FIG. 5A).

Figure 5B:
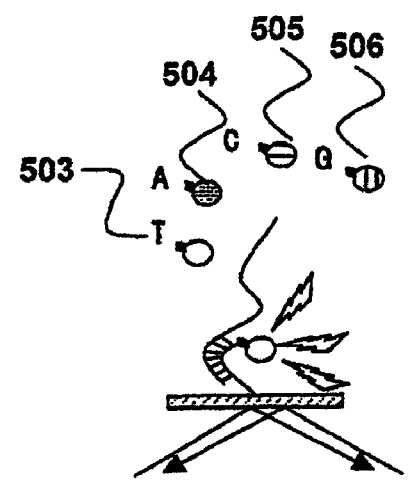
Figure 5C:
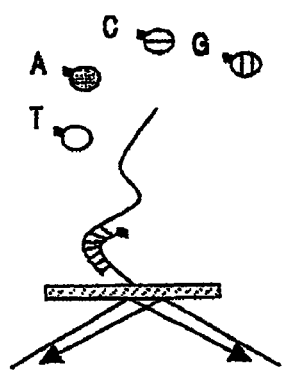
Figure 5D:
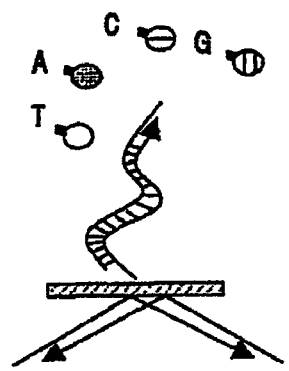

Here, the base 503 is thymine modified with dye emitting infrared fluorescence, the base 504 is adenine modified with dye emitting green fluorescence, the base 505 is cytosine modified with dye emitting red fluorescence, and the base 506 is guanine modified with dye emitting orange fluorescence. By subjecting the substrate to total-internal-reflection illumination with the Ar-ion laser and the laser diode as the excitation light sources 507 and 508, whenever a base is incorporated in the DNA strand and the complementary strand is elongated, light corresponding to the incorporated base is excited and emitted in the evanescent field on the substrate (FIG. 5B).

When dye is photobleached or separated apart, the fluorescence emission disappears (FIG. 5C) and the next base is introduced. By repeating the same process, the extension proceeds (FIG. 5D) and, depending on a difference between colors of bright spots emitted at that time, a base sequence is determined by using a difference between strengths of signals input in the image sensors 131 to 134.

Hereinafter, a measurement process will be described with reference to a flow chart of FIG. 6.

The prism 101 is separated from the sample stage 109 in advance. The sample substrate 106 is fixed to the sample stage 109 (Step 601) and the sample driver 110 drives the sample stage 109 to incline the sample substrate 106 with respect to an opposing surface of the prism 101 with regard to the α axis (Step 602). Thus, it becomes difficult for bubbles to be introduced between the matching liquid 104 filled in the well of the prism 101 and the sample substrate 106.

Next, the well of the prism 101 is manually filled with the matching liquid 104 (Step 603), and the matching liquid 104 in the well slowly approaches to the inclined sample substrate 106 using the Z axis of the prism driver 103 until the matching liquid 104 contacts the sample substrate 106 (Step 604). Alternatively, the filling of the matching liquid 104 may be carried out by opening/closing of a valve of a mechanism for injecting/discharging the matching liquid 104 in/from the prism 101, as will be described later in Embodiment 6.

In addition, the prism driver may include a coarse motion mechanism used when the matching liquid 104 is distant from the sample substrate 106 and a fine motion mechanism used when the matching liquid 104 is close to the sample substrate 106 for improvement of operability. In this case, position detecting means such as a sensor may be provided to detect a distance from a surface of the prism 101 or a surface of a matching liquid 104 layer to the sample substrate 106, and the controller 135 may perform control of switch to the fine motion mechanism when it becomes close to a predetermined position. Although it is illustrated here that the matching liquid 104 contacts the sample substrate 106 by the prism driver 103, these mechanisms may be provided in the sample driver 110.

Thereafter, the sample substrate 106 inclined from the α axis of the sample driver 110 is returned to be horizontal with respect to the matching liquid 104 (Step 605). Thus, the matching liquid 104 is equally filled on the opposing surface of the sample substrate 106. A series of driving operations by the sample driver 110 and the prism driver 103 is automatically performed by the controller 135.

Next, an operation of immobilizing a complex of a DNA single strand and a primer on the substrate (Step 606) using a biotin-avidin binding is performed as follows. A container filled with tris-buffer including biotinylated BSA is equipped as an inflow container 136, and the surface of the sample substrate 106 is coated with the biotinylated BSA by flowing the solution from an inflow path 107 to an outflow path 108. A surplus solution coming out of the outflow path 108 is stored in a waste solution container 137. In order to remove floating biotinylated BSA not coated on the surface of the sample substrate, the inflow container 136 is replaced with a tris-buffer solution container and a cleaning operation to flow a sufficient amount of solution is performed. Hereinafter, likewise, a streptavidin solution and a complex solution of a biotinylated DNA main chain labelled with dye emitting red light and a primer are flown in order and are immobilized. After flowing the solutions, a cleaning operation is performed (Step 606).

For observation of fluorescence of single molecules, shutters 139 and 140 are opened to subject the sample substrate 106 to total-internal-reflection illumination with the Ar-ion laser and the laser diode (Step 607), and a fluorescence image of the image sensors 131 to 134 projected in the controller 135 is focused using a driver 138 of the objective lens driver 138 while viewing the fluorescence image (Step 608). The sample substrate 106 is moved to a region to be observed using the X and Y axes of the sample driver 110 (Step 609) and a position of the complex of the DNA single strand and the primer from an emission bright spot is checked. A reaction starts by introducing a reaction solution containing a fluorescently labelled base and an enzyme from the inflow container 136 (Step 610), and at the same time, a base extension reaction is measured in real time by continuously recording 5000 image data in the controller 135 at a frame rate of 10 frames/sec.

When the sample substrate 106 is taken out, the prism 101 is slowly moved downward using the Z axis of the prism driver 103 until the matching liquid 104 is detached from the sample substrate 106. At this time, by inclining the sample substrate 106 from the α axis of the sample stage 109, the matching liquid 104 attached to the surface of the sample substrate 106 can be easily taken out using surface energy of the matching liquid 104 when the prism 101 is moved downward. After detaching the prism 101, the detached state is maintained for a certain period of time, or a portion of the substrate is somewhat dipped in the liquid surface to absorb liquid drops by a surface tension of the matching liquid, or after confirming that the matching liquid 104 does not flow out of the sample substrate 106 and returning the α axis to the horizontal position, the sample substrate 106 is detached from the sample stage 109 and a new sample substrate 106 is mounted on the sample stage 109.

Although it is illustrated here that the matching liquid 104 is detached from the sample substrate 106 using the prism driver 103, the matching liquid 104 may be detached from the sample substrate 106 using the sample driver 110.

Although one flow channel is provided in the sample substrate in this embodiment, a plurality of samples may be continuously measured when the inflow path 107 and the outflow path 108 are provided in each of a plurality of flow channels and the Steps 606 to 612 are repeated.

With the structure of Embodiment 1, by improving the operability of the matching liquid, difficulty in measurement related to the matching liquid operation can be overcome, the stable measurement can be repeated, and time taken from measurement preparation to measurement completion can be shortened.

Embodiment 2

Next, Embodiment 2 shows an example of measurement by a high aperture-oil immersion type objective lens.

A fluorescent signal from a single fluorescent molecule is weak. Thus, if a background is high or noise derived from an apparatus is large, it is difficult to detect emission bright spots. Therefore, detecting means having higher sensitivity, such as an objective lens with high numerical aperture, is required.

However, since an objective lens with numerical aperture of 1.3 or above is required to be used in an oil immersion state, there is a need to fill the immersion oil between a sample substrate and the objective lens. At that time, operability is poor, immersion oil flows around to make an apparatus dirty, or it takes a long time for a filling operation. Further, when the determination in Embodiment 1 is automated, an immersion oil filling device is required, thereby increasing the burden in terms of space and cost.

Embodiment 2 of the present invention provides means to overcome the above problem. Embodiment 2 has substantially the same basic configuration as Embodiment 1.

FIG. 7 is a sectional view including an excitation light path in the vicinity of the prism of FIGS. 1A and 1B. A well is filled with immersion oil used for an oil immersion type objective lens 703 and the immersion oil is also used as a matching liquid 702 for both a sample substrate 704 and a prism 701.

As shown in FIG. 7, in order to immerse the sample substrate 704 and a lead end of the objective lens 703 in the matching liquid 702, the sample substrate 704 is pushed and fixed to a sample stage 706 by means of a sample supporting member 705, as in Embodiment 1, the prism 701 filled with the matching liquid 702 approaches to the sample substrate 704 until the prism 701 contacts the sample substrate 704, and the matching liquid 702 is supplied from a matching liquid container 708 through a nozzle 709 fixed to the objective lens 703 by opening a small valve 707. Although the sample substrate 704 may be immersed by continuously moving the prism 701 upward without supply of the matching liquid 702 through the nozzle 709, further movement of the prism is difficult due to surface energy around the matching liquid 702 and the sample substrate 704, which may result in poor operability.

Accordingly, this embodiment provides a mechanism in which the prism 701 is moved upward in the operation described in Embodiment 1, it is checked that the matching liquid 702 contacts the sample substrate 704 without mixture of bubbles, and then the matching liquid 702 is supplied from the nozzle 709 provided above the sample substrate 704. Although it is shown here that the matching liquid 702 is supplied through the nozzle 709 after the matching liquid 702 contacts the sample substrate 704, the matching liquid 702 may be supplied before the matching liquid 702 contacts the sample substrate 704. In this case, however, since the amount of the matching liquid 702 used increases before the contact compared to after the contact, a running cost increases. In addition, if the bubbles should be mixed by the supply of the matching liquid 702 from the nozzle 709, it means that the upper surface of the sample substrate 704 already gets wet with the matching liquid 702, and thus it is difficult to check this mixing of the bubbles by visual observation.

With the apparatus of this embodiment, by doubling as the immersion oil for the objective lens 703 and the matching liquid 702 for the sample substrate 704 and the prism 701, the operability of the immersion oil becomes improved and a high sensitivity measurement in the high aperture objective lens becomes possible.

Embodiment 3

In Embodiment 1, the excitation light sources 111 and 112 are provided in different light paths and the excitation light is incident from both sides of the prism 101, as shown in FIG. 1A. If a dichroic mirror 1602 is placed before a mirror 1601 and it is possible to make excitation light paths from two light sources 1603 and 1604 equal, as shown in FIG. 16, it is possible to reduce costs of optical components such as a condensing lens 1609, mirrors and so on and make an apparatus compact.

However, if the excitation light is incident from the same plane of a prism 1605 with the above equal light paths, deviation of a position of evanescent irradiation from light sources having different wavelengths increases due to a refraction angle difference at an interface between the prism 1605 and the matching liquid 1606 depending on a wavelength, along with a distance between the sample substrate 1607 and the prism 1605.

FIG. 17A illustrates respective light paths of when excitation light having wavelengths $\lambda_1$ and $\lambda_2$ transmits a prism 1701 in the same light path, the excitation light is incident into a matching liquid 1702 at an incidence angle $\theta_p$ satisfying the conditional Equation 1, and the incident light is totally reflected at an interface between a sample substrate 1703 and a sample solution 1704. Here, since the excitation light travels in parallel to an X-Z axial plane, a deviation occurs in only the X axis direction.

In FIG. 17A, the reason why the two excitation lights travel along different light paths after being incident into the matching liquid 1704 is that there is a difference in refractive index between the prism 1701, the matching liquid 1702 and the sample substrate 1703 depending on the wavelength, that is, there is a difference in refraction angle therebetween. In FIG. 17A, assuming that an incidence position and an incidence angle $\theta_p$ at the excitation wavelength $\lambda_1$ from the prism 1701 to the matching liquid 1702 are the same as those at the excitation wavelength $\lambda_2$, a deviation $\Delta l$ of an evanescent irradiation position is obtained by the sum of a deviation $\Delta l_m$ occurring when the excitation light transmits the matching liquid 1702 and a deviation $\Delta l_s$ occurring when the excitation light transmits the sample substrate 1703 according to the following Equation 7:

$$\Delta l = \Delta l_m + \Delta l_s \quad \text{[Equation 7]}$$

Where, in order to obtain $\Delta l_m$ and $\Delta l_s$, refractive indexes at the prism 1701, the matching liquid 1702 and the sample substrate 1703 of the excitation light having the wavelengths $\lambda_1$ and $\lambda_2$ are defined as $n_p(\lambda_1)$, $n_p(\lambda_2)$, $n_m(\lambda_1)$, $n_m(\lambda_2)$, $n_s(\lambda_1)$, and $n_s(\lambda_2)$, respectively, and thicknesses of the matching liquid 1702 and the sample substrate 1703 are defined as $\Delta_m$ and $\Delta_s$, respectively (see FIG. 17A). At this time, transmission optic angles $\theta_{m1}$ and $\theta_{m2}$ of the excitation light having the wavelengths $\lambda_1$ and $\lambda_2$ from the prism 1701 to the matching liquid 1702 are given according to Snell's law, as follows:

$$\theta_{m1} = \sin^{-1}((n_p(\lambda_1)/n_m(\lambda_1))\sin(\theta_p)) \quad \text{[Equation 8]}$$

$$\theta_{m2} = \sin^{-1}((n_p(\lambda_2)/n_m(\lambda_2))\sin(\theta_p)) \quad \text{[Equation 9]}$$

Accordingly, $\Delta l_m$ is expressed as follows:

$$\Delta l_m = \Delta m \times |\tan(\theta_{m1}) - \tan(\theta_{m2})| \quad \text{[Equation 10]}$$

Likewise, arranging Equations 8 to 10, $\Delta l_s$ is expressed as follows:

$$\Delta l_s = \Delta s \times |\tan(\sin^{-1}((n_m(\lambda_1)/n_s(\lambda_1))\sin(\theta_{m1}))) - \tan(\sin^{-1}((n_m(\lambda_2)/n_s(\lambda_2))\sin(\theta_{m2})))| \quad \text{[Equation 11]}$$

Accordingly, putting values of Equations 10 and 11 into Equation 7, the deviation $\Delta l$ of the evanescent irradiation position can be obtained.

FIG. 17B shows a plotting diagram of the deviation $\Delta l$ of the evanescent irradiation position calculated with respect to thickness Δm of the matching liquid 1702 when excitation light having wavelengths λ₁=488 nm and λ₂=633 nm is incident into the general prism 1701 made of S-BAL14, quartz or BK7. Parameter values used for the calculation are listed in a table of FIG. 17C. In the table, the incidence angle $\theta_p$ is the maximum value (critical angle) satisfying the Equation 1.

A case where the two excitation light paths in Embodiment 1 are arranged to be the same as shown in FIG. 16 is considered. Since the thickness of the sample supporting member 1608 (thickness of a screw head portion and a polycarbonate plate) is about 3.5 mm, a distance between the sample substrate 106 and the prism 1605 is a minimum of 4 mm. In this case, according to FIG. 17C, the deviation of evanescent irradiation positions of two excitation lights for any material of the prism 1701 becomes about 0.3 mm or above. As a condition for confirming two evanescent irradiation positions in a measurement field of view, the above position deviation is required to be smaller than the sum of an irradiation region diameter and a field of view size. Since a field of view size is about φ100 μm and an irradiation region diameter is 120 μm in Embodiment 1, the condition becomes 0.22 μm or below. Accordingly, if there occurs an irradiation position deviation of about 0.3 mm or above, the minimum of one evanescent irradiation position is out of the field of view. Accordingly, although an evanescent irradiation region is required to be moved by adjusting an angle of the light sources 1603 and 1604 or the mirror 1615, since the irradiation region can not be viewed by visual observation if the evanescent irradiation position is out of the field of view, it is very difficult to adjust an optical axis. In other words, if irradiation is made from the same path as shown in FIG. 16 in the shape of the prism in Embodiment 1, it may take much time for adjustment of the optical axis.

Another problem is a reflected component of the excitation light, which is produced at an interface between the prism 101, the matching liquid 104 and the sample substrate 106. As a difference in refractive index between these three materials increases, a loss by reflection increases, which may result in reduction of excitation strength. In addition, if strength of reflected light is high, reflection repeated around the prism may enter an observation region, which may result in increase of background light and hence reduction of measurement sensitivity. Nonetheless, although refractive indexes of the prism 101, the matching liquid 104 and the sample substrate 106 are required to be similar to one another, the material of the sample substrate 106 is limited to those such as synthetic quartz which does not emit fluorescent light for an excited wavelength.

Accordingly, not only is the material of the prism 101 limited, but also a manufacture cost may increase such as in the case of synthetic quartz. In the present invention, since a material with a size as large as to contain the sample substrate 106 is used, the manufacture cost problem cannot be ignored.

This embodiment provides a prism configuration to overcome the above two problems. This embodiment has substantially the same basic configuration as Embodiment 1. FIG. 8A is a sectional view including excitation light paths around the prism of FIG. 1. An inclined plane in parallel to an outer side of a prism 801 is provided in the bottom of a well. An angle of the inclined plane is set such that excitation light is totally reflected on a surface of a sample substrate 802 when the excitation light is incident perpendicular to the inclined plane. That is, the angle β of the inclined plane, defined in FIG. 8B, satisfies the following Equation 2.

$$\beta > \sin^{-1}(n_{aq}/n_m) \quad \text{[Equation 2]}$$

Where, $n_{aq}$ is a refractive index of a sample solution 803 and $n_m$ is a refractive index of a matching liquid 804. With the configuration of this embodiment, since the excitation light is incident perpendicular to the inclined plane of the prism 801 and the well bottom, there occurs no deviation of light paths depending on a wavelength at the interface even if a plurality of kinds of light sources are mixed in the same light path. In this embodiment, as a mechanism for confirming the perpendicular incidence of the excitation light, an aperture iris 809 having a diameter aperture substantially as the same as a diameter of the excitation light is disposed at a light source side of a condensing lens 808. If the excitation light is perpendicularly incident, since the reflected light incident into the surface of the prism 801 returns to the direction of the light source substantially in the same light path as the light incidence, the returning light beamed on the aperture iris 809 can be confirmed. According to the above method, since the evanescent irradiation region can be put near the field of view of the objective lens 807, an evanescent region can be set within the field of view only by finely adjusting an angle of the light sources 1603 and 1604 or the mirror 1615. Although it is shown here that the aperture iris 809 is disposed at the light source side of the condensing lens 808, the aperture iris 809 may be disposed at the light source side of the prism or mirror 1601. In addition, since the perpendicularity of the light incidence is an indicator to alleviate the trouble of positioning of the evanescent irradiation region, if the incidence angle is deviated from the perpendicularity, the inherent effect of this embodiment does not disappear.

Next, an effect of the reflected light will be described.

FIG. 9A shows a light incidence angle $\theta_i$ and a light transmission angle $\theta_t$ from a prism 901 having a refractive index $n_p$ to a matching liquid 902 having a refractive index $n_m$.

According to Fresnel's formula, reflectivities of p-polarization whose electric field vector is in parallel to an incidence plane and s-polarization whose electric field vector is perpendicular to the incidence plane are as follows:

i) If $\theta_i \neq 0$, $$(p\text{-polarization reflectivity})=(\sin(\theta_i-\theta_t)/\sin(\theta_i+\theta_t))^2 \quad \text{[Equation 3]}$$

$$(s\text{-polarization reflectivity})=(\tan(\theta_i-\theta_t)/\tan(\theta_i+\theta_t))^2 \quad \text{[Equation 4]}$$

ii) If $\theta_i=0$, $$(p/s\text{-polarization reflectivity})=((n_1-n_2)/(n_1+n_2))^2 \quad \text{[Equation 5]}$$

Where, the light transmission angle $\theta_t$ is obtained as follows according to Snell's law.

$$n_p \sin\theta_i = n_m \sin\theta_t \quad \text{[Equation 6]}$$

Therefore, according to Equations 3 to 6, the reflectivity when the matching liquid 902 is glycerol (refractive index $n_m$=1.47) and the material of the prism 901 is S-BSL14 (refractive index $n_p$=1.57) is as shown in FIG. 9B, as in Embodiment 1. As a result, when the light is perpendicularly incident from the prism 901 into the matching liquid 902 ($\theta_i$=0), reflected light becomes minimal and then slowly increases.

When the reflected light enters an observation region, its strength is required to be limited to 1 μW or below. Since a minimum of two times of reflection on the surface of the prism is required, when reflectivity to allow light strength to be 0.3 μW or below at these two times of reflection is assumed as an allowable range, since incidence light power of the general single molecule fluorescence measurement is only 50 μW, it is believed that reflectivity of 0.2% or below is acceptable.

An allowable range of the incidence angle $\theta_i$ when the material of the prism 901 of FIG. 9B is S-BLS14 and the matching liquid 902 is glycerol is 0 to 31 degrees. An allowable range of $\theta_i$ when the material of the prism 901 is BK7 ($n_p$=1.52) is 0 to 53 degrees. An allowable range of $\theta_i$ when the material of the prism 901 is quartz ($n_p$=1.46) and the matching liquid 902 is immersion oil ($n_m$=1.52) is 0 to 45 degrees. Since any of these specified angles is an incidence angle from the prism 901 into the matching liquid 902, when this incidence angle is changed to an incidence angle from air into the prism 901, an allowable range satisfying the above three combinations becomes 0 to 54 degrees. It is here noted that the total reflection condition of Equation 1 is required to be considered.

Next, an allowable angle of parallism of the well bottom of the prism and the excitation light incidence plane will be described by way of an example of a prism made of S-BAL14 which has three 60° equilateral surfaces each having a size of 60 mm×50 mm, which was used in Embodiment 1. When the excitation light is perpendicularly incident, all of three β angles in FIG. 8B are 60 degrees. Here, for the sake of convenience, for the three β angles, it is assumed that an angle formed between the excitation light incidence plane and the matching liquid surface is $\beta_1$, an angle formed between the well bottom of the prism and the matching liquid surface is $\beta_2$, and an incidence angle of the excitation light into the sample substrate is $\beta_3$. An allowable angle of $\beta_1$ when glycerol (refractive index: 1.47) is used as the matching liquid and the excitation light is perpendicularly incident into the prism is obtained. Here, it is assumed that $\beta_2$=60 degrees (constant). First, when $\beta_1$ decreases by $\Delta\beta_1(-)$ degree, an allowable angle is considered. Since $\beta_3$>57.9 degrees according to the total reflection condition of Equation 1, it is established that the incidence angle $\theta_i$ from the prism into the matching liquid is smaller than 1.97 degrees according to Snell's law of Equation 8 or 9. Next, an allowable angle of the perpendicular incidence is considered. According to the allowable area of the above-obtained incidence angle $\theta_i$ to neglect an effect of the reflected light when S-BSL14 is used for the prism 901 and glycerol is used as the matching liquid 902, it is obtained that $\Delta\beta_1(+)$<31 degrees. From the above, an allowable angle of deviation of the parallism of the well bottom of the prism and the excitation light incidence plane becomes −1.97 to +31 degrees.

As described above, with the configuration of this embodiment, although the best effect is obtained when the well bottom of the prism is in substantial parallel to the excitation light incidence plane to satisfy the above parallism condition and the excitation light is perpendicularly incident, the excitation light may be incident in a range of 0 (perpendicular) to 54 degrees with respect to the light incidence plane of the prism even if the light is deviated from the perpendicularity. It is here noted that the total reflection condition of the Equation 1 is required to be considered. In addition, deviation of the parallism of the well bottom of the prism and the excitation light incidence plane is preferably −2 to +30 degrees. Under such a condition, since the prism material is not required to meet a refractive index of the matching liquid and thus a width of selection of the material is widened, the manufacture cost can be reduced.

Accordingly, it can be seen that the two above-mentioned problems can be overcome by this embodiment in which the inclined plane in substantial parallel to the outer side of the prism 801 is provided in the well bottom and the excitation light is incident substantially perpendicular to the inclined plane. This embodiment may be incorporated into Embodiment 1 or 2.

Embodiment 4

Embodiment 4 of the present invention has substantially the same basic configuration as Embodiment 1 except that projections 1002 are provided in a well bottom of a prism 1001 as shown in FIG. 10A. The projections 1002 can be used as a guide when the prism 1001 approaches to a sample substrate to adjust a relative position therebetween. In addition, since the prism 1001 and the opposing surface of the sample substrate can be maintained in parallel with good reproducibility, it is possible to suppress variation of evanescent irradiation strength due to deviation of a relative angle therebetween. In addition, it is possible to prevent close adhesion of the sample substrate and the prism and thus facilitate detachment of the prism from the sample substrate.

Although the projections are prepared by adhering pillar-shaped PMDSs, as denoted by 1002 in FIG. 10B, to the surface of the prism, with their height adjusted as the same, the projections may be two hog-backed projections, as denoted by 1003 in FIG. 10C, or doughnut-shaped projections lacking a part. In a case of doughnut-shaped projections, if their sections are completely circular, since air may be introduced between the matching liquid and the sample substrate when the matching liquid is filled, thereby making a measurement difficult, the doughnut-shaped projections preferably have a section similar to that of the projections of FIG. 10B. In addition, adhesion portions 1004 of the projections 1002 are curved to make bubbles difficult to be attached, as shown in an enlarged view of FIG. 10A. The material for the projections may be hard plastic such as acryl as well as elastic resin such as PDMS. This embodiment may be incorporated into Embodiment 1 or 2.

Embodiment 5

Embodiment 5 of the present invention has substantially the same basic configuration as Embodiment 1 except that a liquid leakage prevention groove 1102 is provided in a wall forming a well of a prism 1101 as shown in FIG. 11A. Even if the prism 1101 is inclined or impacted with the prism 1101 filled with a matching liquid 1103 and thus the matching liquid 1103 flows out along the surface of the prism 1101, the matching liquid 1103 can be stopped in the groove 1102. As a structure to achieve the same effect, a liquid leakage preventing step 1105 such as prism 1104 as shown in FIG. 11B may be provided. In the preparation, although two small and large rectangular PDMS frames are mounted on a plane of the prism 1101, plastic material such as acryl or glass material may be processed into a shape of frame and may be used. Of course, the plane of the prism 1101 may be cut to replace the frames. This embodiment may be incorporated into any of Embodiments 1 to 4.

Embodiment 6

Embodiment 6 of the present invention has substantially the same basic configuration as Embodiment 1 except that an inlet 1203 and an outlet 1204 for exchanging matching liquid 1202 are provided in a wall forming a well of a prism 1201, as shown in FIG. 12. Since the inlet 1203 is connected to a matching liquid container 1205 storing a new matching liquid, the matching liquid may flow to exchange the matching liquid 1202 in the well by opening/closing a valve 1206. The used matching liquid 1202 is stored in a waste matching liquid container 1207. The inherent effect of this embodiment is to simplify exchange of an old matching liquid. This embodiment may be incorporated into any of Embodiments 1 to 5.

When this embodiment is incorporated into Embodiment 2, the same matching liquid container as the matching liquid container 708 and 1205 may be used.

Embodiment 7

Embodiment 7 of the present invention has substantially the same basic configuration as Embodiment 1. FIG. 13A shows a prism 1301 and its vicinity. This embodiment includes a temperature adjusting unit 1303 for adjusting temperature of a matching liquid 1302. The temperature of the temperature adjusting unit 1303 is adjusted by a temperature controller 1304 and the temperature of the matching liquid 1302 may be monitored by a temperature sensor 1305. The temperature controller 1304 may be also used as the controller 135 in Embodiment 1. In the temperature adjusting unit 1303, a heat generating film formed of an ITO film having thickness of about 0.3 mm, which can be heated up to 70° C., is attached to a well bottom of the prism 1301. In addition, the temperature adjusting unit 1303 may be in the form of a wire such as a nichrome wire or strip. In addition, the temperature of the matching liquid 1302 may be adjusted by sandwiching the prism 1301 at both sides with a temperature adjusting unit 1306, as shown in FIG. 13B, or by circulating the matching liquid 1302 within a temperature adjusting unit 1307 by connecting a pipe to wall surfaces of both ends of the well, as shown in FIG. 13C. The inherent effect of this embodiment is to control temperature with little unevenness by controlling the temperature of a sample substrate through the matching liquid. Particularly, in a case of elongation reaction as in Embodiment 1, although reaction temperature is required to increase up to 70° C. in order to raise activity of an enzyme, an elongation reaction efficiency is varied depending on a position of the sample substrate if there is unevenness in temperature, which may result in a serious problem due to remarkable deterioration of a measurement efficiency. For that account, this embodiment aims at and can achieve high throughput of a real time DNA sequencing method. This embodiment may be incorporated into any of Embodiments 1 to 6.

Embodiment 8

Embodiment 8 of the present invention has substantially the same basic configuration as Embodiment 1 except that a well retaining a matching liquid 1402 is formed on a sample substrate 1401 fixed to a sample stage 1408 in a sample supporting member 1410 by adding a matching liquid holding member 1403. In addition, in this embodiment, no well is provided on a prism 1404 side. FIG. 14B is a sectional view including an excitation light path of FIG. 14A. The prism 1404 is immersed in the matching liquid 1402 retained in the well and then the same measurement as Embodiment 1 is performed. In this embodiment, since a well surface opposing to the prism 1404 is required to be a top surface, an objective lens 1405 opposing to a fluorescence detection side is arranged below the sample substrate. Other components have the same relative position relation as those as described above except that positions of components of an irradiation system and a detection system are vertically reversed. The sample stage 1408 is driven by a sample driver 1409.

The sample substrate 1401 is prepared by together attaching two substrates, one being quartz glass of 50 mm×40 mm formed on a surface (upper surface) opposing to the prism 1404 and another being a PDMS substrate (having the same size as that of the upper surface) formed with a flow channel on a lower surface. In addition, instead of the above materials, the sample substrate 1401 may employ materials having absorptiveness and self-fluorescence to an excitation wavelength, which are as low as to have no effect on a measurement. The well retaining the matching liquid 1402 is prepared by adhering matching liquid holding members 1403 and 1502, which are formed of an acryl frame having a surface of 25 mm×25 mm and a height of 5 mm and serve as a wall of the well, on the sample substrate 1501, as shown in FIG. 15A. The material of the matching liquid holding members 1403 and 1502 may be hard plastic as well as soft resin such as silicon or PDMS. In addition, the well may be formed by adhering the matching liquid holding members 1403 and 1502 having a vessel shape as shown in FIG. 15B to the sample substrate 1401 and 1501 or by providing a puddle by cutting the sample substrates 1401 and 1501 as shown in FIG. 15C. Although this embodiment uses a 60° equilateral prism made of S-BAL14 and having a surface of 10 mm×15 mm as the prism 1404, a size as large as to be contained in the well and the material may be any glass such Bak4, quartz or the like, resin such as PDMS or the like, or other materials as long as they have low absorptiveness and self-fluorescence to an excitation wavelength. The inherent effect of this embodiment is to reduce a prism manufacture cost since this embodiment can provide a prism smaller than that of Embodiment 1.

The present invention can be applied to a DNA sequencer using an extension reaction, a DNA micro array reader of a total reflection fluorescent type, etc.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A fluorescence detection apparatus comprising:
    a substrate having a surface on which fluorescently labeled biomolecules are immobilized;
    a sample holding unit that holds said substrate;
    at least one light source that irradiates the substrate with light so that an evanescent field is produced from said substrate;
    a prism disposed on an optical path of the light from said light source, said substrate and said prism being separated from each other;
    a light dividing unit that divides light emitted from said biomolecules for each wavelength;
    a sensor that detects the light divided by said light dividing unit; and
    a controller that processes the light detected by said sensor,
    wherein said prism includes a unit that retains matching liquid to form a liquid layer of said matching liquid in which said substrate is immersed.

2. The fluorescence detection apparatus according to claim 1, wherein said controller inclines said sample holding unit with respect to a surface of said matching liquid layer when the substrate contacts said matching liquid layer.

3. The fluorescence detection apparatus according to claim 1, wherein a surface of said prism, said surface opposing to said substrate, is in parallel to a surface into which the light from the light source is incident,
    wherein an incident angle β from said prism into said matching liquid layer satisfies the following equation, $$\beta > \sin^{-1}(n_{aq}/n_m)$$

where, $n_{aq}$ represents a refractive index of a sample solution containing the biomolecules and $n_m$ represents a refractive index of the matching liquid, and wherein the light from said light source is incident substantially perpendicular to a surface of said prism.

4. The fluorescence detection apparatus according to claim 1, wherein said light dividing unit includes a dichroic mirror and a plurality of image sensors.

5. The fluorescence detection apparatus according to claim 1, further comprising a unit that flows a solution including at least one kind of biomolecule on said substrate.

6. The fluorescence detection apparatus according to claim 1, further comprising an objective lens that passes the light emitted from said biomolecules,
wherein immersion oil for objective lens is used as said matching liquid.

7. The fluorescence detection apparatus according to claim 1, wherein projections are formed on the bottom of a surface on which said matching liquid layer is formed in said prism, and opposing surfaces of said prism and said substrate are in parallel to each other when said substrate is pressed against said prism.

8. The fluorescence detection apparatus according to claim 1, wherein said wall includes a groove that receives said matching liquid.

9. The fluorescence detection apparatus according to claim 1, further comprising injecting means that injects said matching liquid into said prism and discharging means that discharges said matching liquid from said prism.

10. The fluorescence detection apparatus according to claim 1, further comprising a temperature adjusting mechanism that adjusts temperature of said matching liquid injected into said prism,
wherein said temperature adjusting mechanism is controlled by said controller.

11. A fluorescence detection apparatus comprising:
a substrate having a surface on which fluorescently labeled label biomolecules are immobilized;
a sample holding unit that holds said substrate;
a sample driving unit that drives said sample holding unit;
at least one light source that irradiates the substrate with light from a back side of said substrate so that an evanescent field is produced from said substrate;
a prism disposed on an optical path of the light from said light source, said substrate and said prism being separated from each other;
a prism driving unit that drives said prism;
a light dividing unit that divides light emitted from said biomolecules;
a sensor that detects the light divided by said light dividing unit; and
a controller that processes the light detected by said sensor,
wherein said prism includes a wall that retains matching liquid to form a liquid layer of said matching liquid in which said substrate is immersed, and
wherein said controller inclines said sample holding unit with respect to a surface of said matching liquid layer when the substrate contacts said matching liquid layer.

12. The fluorescence detection apparatus according to claim 11, wherein said controller controls said prism driving unit to adjust a distance between said substrate and said prism.

13. The fluorescence detection apparatus according to claim 12, wherein said prism driving unit includes a coarse movement mechanism and a fine movement mechanism.

14. The fluorescence detection apparatus according to claim 11, wherein a surface of said prism, said surface opposing to said substrate, is in parallel to a surface into which the light from the light source is incident, wherein an incident angle $\beta$ from said prism into said matching liquid layer satisfies the following equation, $$\beta > \sin^{-1}(n_{aq}/n_m)$$

where, $n_{aq}$ represents a refractive index of a sample solution containing the biomolecules and nm represents a refractive index of the matching liquid, and
wherein the light from said light source is incident substantially perpendicular to a surface of said prism.

15. The fluorescence detection apparatus according to claim 11, wherein said light dividing unit includes a dichroic mirror and a plurality of image sensors.

16. The fluorescence detection apparatus according to claim 11, further comprising a unit that flows a solution including at least one kind of biomolecule on said substrate.

17. The fluorescence detection apparatus according to claim 11, further comprising an objective lens that passes the light emitted from said biomolecules,
wherein immersion oil for objective lens is used as said matching liquid.

18. The fluorescence detection apparatus according to claim 11, wherein projections are formed on the bottom of a surface on which said matching liquid layer is formed in said prism, and opposing surfaces of said prism and said substrate are in parallel to each other when said substrate is pressed against said prism.

19. The fluorescence detection apparatus according to claim 11, wherein said wall includes a groove that receives said matching liquid.

20. The fluorescence detection apparatus according to claim 11, further comprising injecting means that injects said matching liquid into said prism and discharging means that discharges said matching liquid from said prism.

21. The fluorescence detection apparatus according to claim 11, further comprising a temperature adjusting mechanism that adjusts temperature of said matching liquid injected into said prism,
wherein said temperature adjusting mechanism is controlled by said controller.

22. A fluorescence detection apparatus comprising:
a substrate having a surface on which fluorescently labeled biomolecules are immobilized;
a sample holding unit that holds said substrate;
a plurality of light sources that emits light having different wavelengths so that an evanescent field is produced from said substrate and the light has the same optical path with respect to a back side of said substrate;
a prism disposed on the optical path of the light from said plurality of light sources, said substrate and said prism being separated from each other;
a light dividing unit that divides light emitted from said biomolecules for each wavelength;
a sensor that detects the light divided by said light dividing unit; and
a controller that processes the light detected by said sensor,
wherein said prism includes a unit that retains a matching liquid to form a liquid layer of said matching liquid in which said substrate is immersed,
wherein a surface of said prism, said surface opposing to said substrate, is in substantial parallel to a surface into which the light from said light source is incident, and
wherein an incidence angle of the light from said light sources with respect to the prism surface is between 0 degree and 54 degrees.

* * * * *